US009610243B2

(12) United States Patent
Clay et al.

(10) Patent No.: US 9,610,243 B2
(45) Date of Patent: *Apr. 4, 2017

(54) CLONIDINE COMPOUNDS IN A BIODEGRADABLE POLYMER

(71) Applicants: Warsaw Orthopedic, Inc., Warsaw, IN (US); Medtronic, Inc., Minneapolis, MN (US)

(72) Inventors: Danielle L. Clay, Collierville, TN (US); Josee Roy, Memphis, TN (US); William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 517 days.

This patent is subject to a terminal disclaimer.

(21) Appl. No.: 13/841,481

(22) Filed: Mar. 15, 2013

(65) Prior Publication Data

US 2013/0216602 A1   Aug. 22, 2013

Related U.S. Application Data

(63) Continuation-in-part of application No. 12/420,197, filed on Apr. 8, 2009, now Pat. No. 8,946,277.

(60) Provisional application No. 61/046,201, filed on Apr. 18, 2008.

(51) Int. Cl.
*A01N 43/50* (2006.01)
*A61K 31/415* (2006.01)
*A61K 9/00* (2006.01)
*A61K 9/20* (2006.01)
*A61K 31/4162* (2006.01)

(52) U.S. Cl.
CPC .......... *A61K 9/0002* (2013.01); *A61K 9/0024* (2013.01); *A61K 9/0085* (2013.01); *A61K 9/204* (2013.01); *A61K 31/4162* (2013.01)

(58) Field of Classification Search
None
See application file for complete search history.

(56) References Cited

U.S. PATENT DOCUMENTS

| | | | |
|---|---|---|---|
| 3,190,802 A | 6/1965 | Zeile et al. | |
| 3,020,660 A | 8/1965 | Zeile et al. | |
| 4,765,974 A | 8/1988 | Tokuda et al. | |
| 5,175,052 A | 12/1992 | Tokuda et al. | |
| 5,447,947 A | 9/1995 | Campbell | |
| 5,484,607 A | 1/1996 | Horacek | |
| 5,633,002 A * | 5/1997 | Stricker et al. | 424/426 |
| 5,635,204 A | 6/1997 | Gervirtz et al. | |
| 5,801,188 A | 9/1998 | Hassenbusch, III et al. | |
| 5,869,100 A | 2/1999 | Horacek | |
| 5,942,503 A | 8/1999 | Jung et al. | |
| 5,942,530 A | 8/1999 | Panetta et al. | |
| 5,945,416 A | 8/1999 | Shannon et al. | |
| 5,980,927 A * | 11/1999 | Nelson et al. | 424/425 |
| 6,030,642 A | 2/2000 | Horacek | |
| 6,147,102 A | 11/2000 | Borgman | |
| 6,248,345 B1 | 6/2001 | Goldenheim et al. | |
| 6,417,184 B1 | 7/2002 | Ockert | |
| 6,534,048 B1 | 3/2003 | Borgman | |
| 6,992,110 B2 | 1/2006 | Kranzler et al. | |
| 7,345,065 B2 | 3/2008 | Gil et al. | |
| 7,507,398 B2 | 3/2009 | Rabinowitz et al. | |
| 7,524,812 B2 | 4/2009 | Ellis et al. | |
| 2002/0058656 A1 | 5/2002 | Ockert | |
| 2002/0094998 A1 | 7/2002 | Burke et al. | |
| 2003/0022926 A1 | 1/2003 | Lavand'Homme | |
| 2004/0028726 A1 | 2/2004 | Fischer et al. | |
| 2004/0101582 A1 | 5/2004 | Wolicki | |
| 2004/0208917 A1 | 10/2004 | Fischer et al. | |
| 2004/0265364 A1 | 12/2004 | Ozturk et al. | |
| 2005/0059744 A1 | 3/2005 | Donello et al. | |
| 2005/0095277 A1 | 5/2005 | Ozturk et al. | |
| 2005/0177135 A1 * | 8/2005 | Hildebrand et al. | 604/890.1 |
| 2006/0173060 A1 | 8/2006 | Chang et al. | |
| 2008/0152709 A1 | 6/2008 | Bortz | |
| 2008/0171075 A1 | 7/2008 | Ozturk et al. | |
| 2010/0159015 A1 * | 6/2010 | Burright et al. | 424/489 |

FOREIGN PATENT DOCUMENTS

| | | |
|---|---|---|
| WO | 2005000278 | 1/2005 |
| WO | 2005110362 A1 | 11/2005 |
| WO | 2006011915 A1 | 2/2006 |
| WO | 2006022611 A2 | 3/2006 |
| WO | 2006101540 A1 | 9/2006 |
| WO | 2008014066 A1 | 1/2008 |
| WO | 2008079868 A1 | 7/2008 |
| WO | 2009100441 A2 | 8/2009 |

OTHER PUBLICATIONS

International Search Report and Written Opinion for Application No. PCT/US2009/040953 mailed Dec. 14, 2009.
Rathnell et al. In a review in Anesthesia and Analgesia 2005; 101:S30-S43.
Syringe Needle Gauge Chart (www.sigmaaldrich.com/chemistry/stockroom-reagents/learning-center/technical-library/needle-gauge-chart.html.

* cited by examiner

*Primary Examiner* — Dennis Heyer
*Assistant Examiner* — Daniel M Podgorski

(57) ABSTRACT

Effective treatments of pain for extended periods of time are provided. Through the administration of an effective amount of clonidine in a drug depot at or near a target site, one can relieve pain caused by diverse sources, including but not limited to spinal disc herniation (i.e. sciatica), spondilothesis, stenosis, discogenic back pain and joint pain. When appropriate drug depot formulations are provided within biodegradable polymers, this pain relief can be continued for at least fourteen days.

9 Claims, 3 Drawing Sheets

CLONIDINE COMPOUNDS IN A BIODEGRADABLE POLYMER

This application claims the benefit of the filing date of and is a continuation-in-part of U.S. application Ser. No. 12/420,197, filed Apr. 8, 2009, entitled "Clonidine Formulations In A Biodegradable Polymer Carrier", which claims the benefit of provisional application No. 61/046,201, filed Apr. 18, 2008, entitled "Clonidine Formulations In A Biodegradable Polymer Carrier." These entire disclosures are hereby incorporated by reference into the present disclosure.

BACKGROUND

Pain is typically experienced when the free nerve endings of pain receptors are subject to mechanical, thermal, chemical or other noxious stimuli. These pain receptors can transmit signals along afferent neurons to the central nervous system and then to the brain. When a person feels pain, any one or more of a number of problems can be associated with this sensation, including but not limited to reduced function, reduced mobility, complication of sleep patterns, and decreased quality of life.

The causes of pain include but are not limited to inflammation, injury, disease, muscle stress, the onset of a neuropathic event or syndrome, and damage that can result from surgery or an adverse physical, chemical or thermal event or from infection by a biologic agent. When a tissue is damaged, a host of endogenous pain inducing substances, for example, bradykinin and histamine can be released from the injured tissue. The pain inducing substances can bind to receptors on the sensory nerve terminals and thereby initiate afferent pain signals. After activation of the primary sensory afferent neurons, the projection neurons may be activated. These neurons carry the signal via the spinothalamic tract to higher parts of the central nervous system.

One known class of pharmaceuticals to treat pain is opioids. This class of compounds is well-recognized as being among the most effective type of drugs for controlling pain, such as post-operative pain. Unfortunately, because opioids are administered systemically, the associated side effects raise significant concerns, including disabling the patient, depressing the respiratory system, constipation, and psychoactive effects such as sedation and euphoria, thereby instituting a hurdle to recovery and regained mobility. Consequently, physicians typically limit the administration of opioids to within the first twenty-four hours post-surgery. Thus, it would be preferable to use non-narcotic drugs that deliver direct, localized pain control at a surgical site.

One pharmaceutical that is known to the medical profession is clonidine, which is widely recognized as an antihypertensive agent that acts as an agonist on the alpha-2-adrenergic receptor and as a neural receptor agonist. In general, clonidine, also referred to as 2,6-dichloro-N-2-imidazolidinyldenebenzenamine ($C_9H_9Cl_2N_3$) may be represented by the following chemical structure:

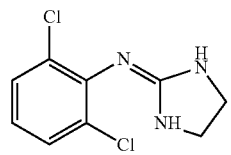 [SMILES: Clc1cccc(Cl)c1N=C1NCCN1]

However, to date clonidine compounds have not been widely appreciated as a localized and effective treatment for pain. Thus, there is a need to develop effective devices and compositions containing clonidine compounds for this application.

SUMMARY

Compositions and methods are provided comprising clonidine or its pharmaceutically acceptable salts that are administered in order to treat pain and/or inflammation. The compositions and methods may for example be used to treat pain due to a spinal disc herniation (i.e., sciatica), spondilothesis, stenosis, osteoarthritis, carpal/tarsal tunnel syndrome, tendonitis, temporomandibular joint disorder (TMJ), discogenic back pain, joint pain or inflammation.

In some embodiments, there is an implantable medical device for reducing or treating pain in a patient in need of such treatment, the implantable medical device comprising clonidine in an amount from about 1.0 wt. % to about 20 wt. % of the implantable medical device, and at least one biodegradable polymer, wherein the implantable medical device releases the clonidine over a period of at least 14 days.

In some embodiments, there is an implantable drug depot for treating chronic pain in a patient in need of such treatment, the implantable medical device comprising clonidine hydrochloride in an amount from about 5.0 wt. % to about 20 wt. % of the implantable drug depot, and at least one biodegradable polymer comprising poly(D,L-lactide), wherein the implantable medical device releases the clonidine over a period of at least 30 days to one year.

In some embodiments, there is a method for treating chronic pain in a patient in need of such treatment, the method comprising administering an implantable drug depot to a target tissue site beneath the skin of the patient, the implantable drug depot comprising clonidine in an amount from about 5.0 wt % to about 20 wt % of the implantable medical device, and at least one biodegradable polymer, wherein the implantable medical device releases the clonidine over a period of at least 14 days.

In some embodiments, the drug depot may: (i) consist of only the clonidine (or one or more of its pharmaceutically acceptable salts) and the biodegradable polymer(s); or (ii) consist essentially of the clonidine (and/or one or more of its pharmaceutically acceptable salts) and the biodegradable polymer(s); or (iii) comprise the clonidine (and/or one or more of its pharmaceutically acceptable salts), and the biodegradable polymer(s) and one or more other active ingredients, surfactants, excipients or other ingredients or combinations thereof. When there are other active ingredients, surfactants, excipients or other ingredients or combinations thereof in the formulation, in some embodiments these other compounds or combinations thereof comprise less than 50 wt. %, less than 40 wt. %, less than 30 wt. %, less than 20 wt. %, less than 19 wt. %, less than 18 wt. %, less than 17 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. %.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
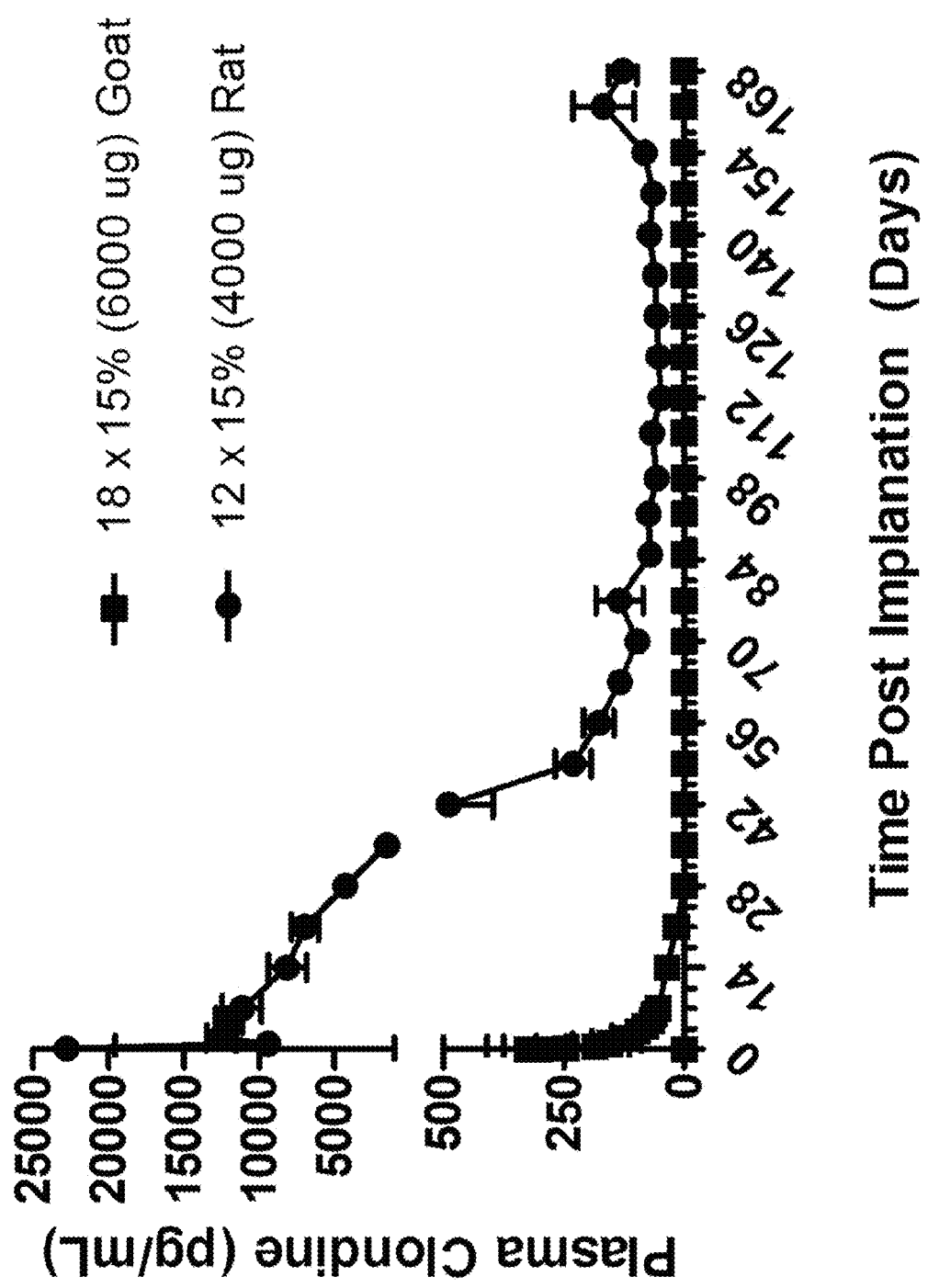
FIG. 1 is a graphic illustration of plasma concentrations of clonidine for over 168 days employing formulations of the present application.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Definitions

It is noted that, as used in this specification and the appended claims, the singular forms "a," "an," and "the," include plural referents unless expressly and unequivocally limited to one referent. Thus, for example, reference to "a drug depot" includes one, two, three or more matrices.

An implantable medical device includes that the device can be implanted into the human body. In various embodiments, the medical device is not implanted into the eye. The medical device allows release of the drug or therapeutic agent. A medical device includes a drug depot, which can be solid, semi-solid or in gel form.

The term "implantable" as utilized herein refers to a biocompatible depot (e.g., device) retaining potential for successful placement within a mammal. The expression "implantable depot" and expressions of the like import as utilized herein refers to an object implantable through surgery, injection, or other suitable means whose primary function is achieved either through its physical presence or mechanical properties.

A "drug depot" is the composition in which the clonidine is administered to the body. Thus, a drug depot may comprise a physical structure (e.g., strip, pellet) to facilitate implantation and retention in a desired site (e.g., a disc space, a spinal canal, a tissue of the patient, particularly at or near a site of chronic pain, etc.). The drug depot (e.g., fiber) may also comprise the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot (e.g., fiber) provides an optimal drug concentration gradient of the therapeutic agent at a distance of up to about 0.01 cm to about 20 cm from the administration site and comprises clonidine. A drug depot (e.g., fiber) may also include a pump or pellet.

A "therapeutically effective amount" or "effective amount" is such that when administered, the drug results in alteration of the biological activity, such as, for example, inhibition of inflammation, reduction or alleviation of pain or spasticity, improvement in the condition through muscle relaxation, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces.

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. Suitable materials for the depot (e.g., fiber) are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The "fiber" of the present application provides a 3-D fiber of interconnecting pores, which acts as a pliant scaffold for cell migration and/or drug release.

As used herein, "fiber" refers to any flexible structure that can be stretched between two points and includes, without limitation, traditional fiber material, single or multiple stranded threads, or a mesh structure. A fiber may also be a strap-like structure with a number of holes in it. A "fiber" may also take the form of an acellular, collagen membrane or other biologic tissue augment, which may provide a scaffold or support matrix for cellular ingrowth to allow soft tissue to reconstruct itself. Fibers may include silk, nylon, linen, cotton, chromic gut, plain gut, cat gut, vicryl, polyglactin, polyester, polypropylene, stainless steel, synthetic polymers having lactic acid or glycolic acid ester linkages subject to hydrolytic degradation to non-toxic tissue compatible absorbable components, including polylactic acid or polyglycolic acid. The fiber may be monofilamentary or braided, absorbable or non-absorbable.

The term "biodegradable" includes that all or parts of the drug depot (e.g., fiber) will degrade over time by the action of enzymes, by hydrolytic action and/or by other similar mechanisms in the human body. In various embodiments, "biodegradable" includes that the depot (e.g., fiber) can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot (e.g., fiber) will be broken down and absorbed within the human body, for example, by a cell or tissue. "Biocompatible" means that the depot (e.g., fiber) will not cause substantial tissue irritation or necrosis at the target tissue site.

In some embodiments, the drug depot (e.g., fiber) has pores that allow release of the drug from the depot (e.g., fiber). The drug depot (e.g., fiber) will allow fluid in the depot (e.g., fiber) to displace the drug. However, cell infiltration into the depot (e.g., fiber) will be prevented by the size of the pores of the depot (e.g., fiber). In this way, in some embodiments, the depot (e.g., fiber) should not function as a tissue scaffold and allow tissue growth. Rather, the drug depot (e.g., fiber) will solely be utilized for drug delivery. In some embodiments, the pores in the drug depot (e.g., fiber) will be less than 250 to 500 microns. This pore size will prevent cells from infiltrating the drug depot (e.g., fiber) and laying down scaffolding cells. Thus, in this embodiment, the drug will elute from the drug depot (e.g., fiber) as fluid enters the drug depot (e.g., fiber), but cells will be prevented from entering. In some embodiments, where there are little or no pores, the drug will elute out from the drug depot (e.g., fiber) by the action of enzymes, by hydrolytic action and/or by other similar mechanisms in the human body. In some embodiments, the drug depot (e.g., fiber) will function to allow influx of cells and tissue and it will function as a scaffold.

The phrases "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a fiber or component thereof, or as the result of metabolic transformation or dissolution of the therapeutic agent(s) or conjugates of therapeutic agent(s).

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

The two types of formulations (sustain release and immediate release) may be used in conjunction. The sustained release and immediate release may be in one or more of the same fiber. In various embodiments, the sustained release and immediate release may be part of separate drug depots. For example a bolus or immediate release formulation of clonidine may be placed at or near the target site and a sustain release formulation may also be placed at or near the same site. Thus, even after the bolus becomes completely accessible, the sustain release formulation would continue to provide the active ingredient for the intended tissue.

In various embodiments, the drug depot can be designed to cause an initial burst dose of therapeutic agent within the first twenty-four to seventy-two hours after implantation. "Initial burst" or "burst effect" "burst release" or "bolus dose" refers to the release of therapeutic agent from the depot (e.g., fiber, pellet, strip, etc.) during the first twenty-four hours to seventy-two hours after the depot (e.g., fiber) comes in contact with an aqueous fluid (e.g., interstitial fluid, synovial fluid, cerebral spinal fluid, etc.). The "burst effect" is believed to be due to the increased release of therapeutic agent from the drug depot. In some embodiments, the drug depot has one or more burst release surfaces that releases about 10%, 15%, 20%, 25%, 30%, 35%, 45%, to about 50% of the drug over 24 or 48 hours.

In alternative embodiments, the drug depot is designed to avoid or reduce this initial burst effect (e.g., by applying an outer polymer coating to the drug depot).

"Treating" or "treatment" of a disease or condition refers to executing a protocol that may include administering one or more drugs to a patient (human, other normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition. In addition, treating or treatment does not require complete alleviation of signs or symptoms, does not require a cure, and specifically includes protocols that have only a marginal effect on the patient. "Reducing pain and/or inflammation" includes a decrease in pain and/or inflammation and does not require complete alleviation of pain and/or inflammation signs or symptoms, and does not require a cure. In various embodiments, reducing pain and/or inflammation includes even a marginal decrease in pain and/or inflammation. By way of example, the administration of the effective dosage of clonidine may be used to prevent, treat or relieve the symptoms of pain and/or inflammation for different diseases or conditions. These disease/conditions may comprise post-operative pain, oral-facial diseases, bursitis, tendonitis, chronic inflammatory diseases, including, but not limited to autoimmune diseases, such as multiple sclerosis, rheumatoid arthritis, osteoarthritis, insulin dependent diabetes (type I diabetes), systemic lupus erythrematosis and psoriasis, immune pathologies induced by infectious agents, such as helminthic (e.g., leishmaniasis) and certain viral infections, including HIV, and bacterial infections, including Lyme disease, tuberculosis and lepromatous leprosy, tissue transplant rejection, graft versus host disease and atopic conditions, such as asthma and allergy, including allergic rhinitis, gastrointestinal allergies, including food allergies, eosinophilia, conjunctivitis or glomerular nephritis. In some embodiments, the drug depot containing the therapeutic agent is not administered in, to or near the eye.

One chronic condition is sciatica. In general, sciatica is an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area. In various embodiments, the clonidine may be used to reduce, treat, or prevent sciatic pain and/or inflammation by locally administering the clonidine at one or more target tissue sites (e.g., nerve root, dorsal root ganglion, focal sites of pain, at or near the spinal column, etc.).

In some embodiments, the drug depot can be used to treat one or more target tissue sites that are involved in conditions/diseases, such as for example, rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, a surgical wound site or an incision site, postoperative pain or the like.

The term "implantable" as utilized herein refers to a biocompatible device (e.g., pellet) retaining potential for successful placement within a mammal. The expression "implantable device" and expressions of the like import as utilized herein refers to an object implantable through surgery, injection, or other suitable means whose primary function is achieved either through its physical presence or mechanical properties.

"Localized" delivery includes delivery where one or more drugs are deposited within a tissue, for example, a nerve root of the nervous system or a region of the brain, or in close proximity (within about 0.1 cm, or preferably within about 10 cm, for example) thereto. For example, the drug dose delivered locally from the drug depot may be, for example, 10%, 20%, 30%, 40%, 50%, 60%, 70%, 80%, 90%, 95%, 99%, or 99.9% less than the oral dosage or injectable dose. In turn, systemic side effects, such as for example, liver transaminase elevations, hepatitis, liver failure, myopathy, constipation, etc. may be reduced or eliminated.

The term "mammal" refers to organisms from the taxonomy class "mammalian," including but not limited to humans, other primates such as chimpanzees, apes, orangutans and monkeys, rats, mice, cats, dogs, cows, horses, etc.

The phrase "pain management medication" includes one or more therapeutic agents that are administered to prevent, alleviate or remove pain entirely. These include anti-inflammatory agents, muscle relaxants, analgesics, anesthetics, narcotics, and so forth, and combinations thereof.

The phrase "release rate profile" refers to the percentage of active ingredient that is released over fixed units of time, e.g., mcg/hr, mcg/day, 10% per day for ten days, etc. As persons of ordinary skill know, a release rate profile may, but need not, be linear. By way of a non-limiting example, the drug depot may be a ribbon-like fiber that releases the clonidine over a period of time.

The term "solid" is intended to mean a rigid material, while, "semi-solid" is intended to mean a material that has some degree of flexibility, thereby allowing the depot (e.g., fiber, strip, pellet, etc.) to bend and conform to the surrounding tissue requirements.

"Targeted delivery system" provides delivery of one or more drugs depots (e.g., fibers, strip, pellet, etc.) at or near the target site as needed for treatment of pain, inflammation or other disease or condition.

The abbreviation "DLG" refers to poly(DL-lactide-co-glycolide).

The abbreviation "DL" refers to poly(DL-lactide).

The abbreviation "LG" refers to poly(L-lactide-co-glycolide).

The abbreviation "CL" refers to polycaprolactone.

The abbreviation "DLCL" refers to poly(DL-lactide-co-caprolactone).

The abbreviation "LCL" refers to poly(L-lactide-co-caprolactone).

The abbreviation "G" refers to polyglycolide.

The abbreviation "PEG" refers to poly(ethylene glycol).

The abbreviation "PLGA" refers to poly(lactide-co-glycolide) also known as poly(lactic-co-glycolic acid), which are used interchangeably.

The abbreviation "PLA" refers to polylactide.

The abbreviation "PEA" refers to poly(ester)amides.

The abbreviation "POE" refers to poly(orthoester). The above polymers or combination of polymers can be in the drug depot (e.g., fiber, strip, pellet, etc.).

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Clonidine Compounds

When referring to clonidine, unless otherwise specified or apparent from context it is understood that the inventors are also referring to pharmaceutically acceptable salts. One well-known commercially available salt for clonidine is its hydrochloride salt. Some other examples of potentially pharmaceutically acceptable salts include those salt-forming acids and bases that do not substantially increase the toxicity of a compound, such as, salts of alkali metals such as magnesium, potassium and ammonium, salts of mineral acids such as hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, and the like.

Further, when referring to clonidine, the active ingredient may not only be in the salt form, but also in the base form (e.g., free base). In various embodiments, if it is in the base form, it may be combined with polymers under conditions in which there is not severe polymer degradation, as may be seen upon heat or solvent processing that may occur with PLGA or PLA. By way of a non-limiting example, when formulating clonidine with poly(orthoesters) it may be desirable to use the clonidine base formulation. By contrast, when formulating clonidine with PLGA, it may be desirable to use the HCl salt form. In some embodiments, the clonidine may be incorporated into a polymer core with a polymer and then coated with the same or different polymer.

Pharmaceutically acceptable salts of clonidine include salts prepared from pharmaceutically acceptable non-toxic bases or acids including inorganic or organic bases, inorganic or organic acids and fatty acids. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethyl amine, tripropylamine, tromethamine, and the like. When the compound of the current application is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Fatty acid salts may also be used, e.g., fatty acid salts having greater than 2 carbons, greater than 8 carbons or greater than 16 carbons, such as butyric, caprioc, caprylic, capric, lauric, mystiric, palmitic, stearic, arachidic or the like.

In some embodiments, in order to reduce the solubility of the clonidine to assist in obtaining a controlled release depot (e.g., fiber, strip, pellet, etc.) effect, clonidine is utilized as the free base or utilized in a salt which has relatively lower solubility. For example, the present application can utilize an insoluble salt such as a fatty acid salt. Representative fatty acid salts include salts of oleic acid or linoleic acid. In preferred embodiments fatty acid salts with between 8 to 20 carbons are used to produce salts with low solubility, such as clonidine palmeate and clonidine stearate. Most preferably, fatty acid salts with between 12 to 18 carbons are used. Other embodiments can utilize a lipid soluble salt of clonidine.

In some embodiments, clonidine can be used with a GABA compound in the drug depot. The GABA compounds used in the treatment methods and in the device include compounds of gamma-aminobutyric acid. Such compounds include gabapentin (2-[1-(aminomethyl)cyclohexyl]acetic acid), pregabalin ((S)-3-(aminomethyl)-5-methylhexanoic acid), vigabatrin (4-aminohex-5-enoic acid), and baclofen (4-amino-3-(4-chlorophenyl)butanoic acid), which are 3'-alkylated GABA compounds. Additional GABA compounds that may be used are described in Satzinger et al., U.S. Pat. No. 4,024,175; Silverman et al., U.S. Pat. No. 5,563,175; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; WO 02/00209); Silverman et al., PCT Publication No. WO 92/09560; Silverman et al., PCT Publication No. WO 93/23383; Horwell et al., PCT Publication No. WO 97/29101, Horwell et al., PCT Publication No. WO 97/33858; Horwell et al., PCT Publication No. WO 97/33859; Bryans et al., PCT Publication No. WO 98/17627; Guglietta et al., PCT Publication No. WO 99/08671; Bryans et al., PCT Publication No. WO 99/21824; Bryans et al., PCT Publication No. WO 99/31057; WO 98/23383; Bryans et al., J. Med. Chem. 1998, 41, 1838-1845; Bryans et al., Med. Res. Rev. 1999, 19, 149-177, US Guglietta et al., WO 99/08670; Bryans et al., WO 99/21824; US Bryans et al., UK GB 2 374 595), Belliotti et al., PCT Publication No. WO 99/31074; Bryans et al., PCT Publication No. WO 99/31075; Bryans et al., PCT Publication No. WO 99/61424; Bryans et al., PCT Publication No. WO 00/15611; Bryans, PCT Publication No. WO 00/31020; Bryans et al., PCT Publication No. WO 00/50027; and Bryans et al., PCT Publication No. WO 02/00209). New classes of GABA compounds, which are bicyclic amino acid derivatives, have been recently described by Bryans et al., PCT Publication No. WO 01/28978; Blakemore et al., PCT Pub. No. WO 02/085839; Blakemore et al., U.S. Pat. No. 5,596,900; and Blakemore et al., PCT Pub. No. WO 02/090318. These disclosures are herein incorporated by reference into the present disclosure.

In one embodiment, the GABA compound comprises 1-{[(alpha-isobutanoyloxyethoxy)carbonyl]aminomethyl}-1-cyclohexane acetic acid, baclofen, vigabatrin, gabapentin, pregabalin, gamma-amino-phosphinic acid or 1-{[(alpha-isobutanoyloxyethoxy)carbonyl]aminomethyl}-1-cyclohexane acetic acid, fengabine, GBL (gamma-Butyrolactone), GHB (gamma-Hydroxybutyric acid, 4-hydroxybutanoic acid or sodium oxybate), picamilon and progabide, (s)-(+)-4-amino-3-(2-methylpropyl) butanoic acid In another embodiment, GABA compounds include pharmaceuticals that can increase locally the available amount of endogenous GABA or GABA analogs following their local or systemic administration. These include pharmaceuticals that interfere with GABA or GABA analog reuptake such as tiagabine, stiripentol, deramciclane, hyperforin or a combination thereof. GABA compounds also include pharmaceuticals that interfere with the degradation of GABA or GABA analogs such as phenelzine, gabaculine, valproate, vigabatrin, lemon balm or a combination thereof.

In some embodiments, the GABA compound is released locally from the device at a dose of from about 0.3 mg/day or about 1.8 mg/day or about 3.6 mg/day to about 180 mg/day or about 360 mg/day. In some embodiments, the GABA compound is released from the device at a dose of 0.75 mg to 16 mg per day. In some embodiments, the initial burst or bolus release is about 2 to 20 times higher from 1 hour to about two weeks than the sustained release daily dose released from the device.

In some embodiments, the GABA compound comprises gabapentin, which is released from the device at a dosage of from about 0.3 mg or 1 mg to about 8 mg, 10 mg, 16 mg or 32 mg per day. In some embodiments, the GABA compound comprises pregabalin, which is released from the device at a dosage of from about 0.1 mg or 0.3 mg to about 1 mg, 3 mg, 5 mg or 10 mg per day. In some embodiments, the clonidine can be released from the depot (e.g., fiber, strip, pellet, etc.) at a dose of 0.002 mg to 16 mg per day.

In some embodiments, the ratio of gabapentin to clonidine would be 300:1. For pregabalin, the ratio would be approximately 100:1. In some embodiments, the drug depot releases 300 mg of pregabalin per day.

The GABA compound compliments the anti-inflammatory and analgesic effect of clonidine in the drug depot.

In some embodiments, the drug depot comprises clonidine that is in the drug depot in an amount of from about 0.1% to about 75% by weight.

In some embodiments, the drug depot comprises both a GABA compound and clonidine in a single formulation. In some embodiments, the GABA compound can be in a separate depot (e.g., drug depot) from the clonidine.

In some embodiments, a GABA compound, a steroid, bupivacaine, lidocaine and/or clonidine can be administered in an immediate release or sustained release liquid by injection before, after, or during the administration of the clonidine depot (e.g., drug depot).

The clonidine and GABA compound or its pharmaceutically acceptable salt may be administered with a muscle relaxant. Exemplary muscle relaxants include by way of example and not limitation, alcuronium chloride, atracurium bescylate, carbamate, carbolonium, carisoprodol, chlorphenesin, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The drug depot may comprise other therapeutic agents in addition to the clonidine and/or GABA compound as well. These therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogs (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as glucocorticoids, antioxidants, such as dithiocarbamate, and other compounds, such as, for example, sulfasalazine.

Examples of therapeutic agents suitable for use also include, but are not limited to an anti-inflammatory agent, an analgesic agent, or an osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, sulindac, tepoxalin or tolmetin; as well as antioxidants, such as dithiocarbamate, steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor (e.g., GDF-5), a LIM mineralization protein, CDMP or progenitor cells or a combination thereof.

Suitable analgesic agents include, but are not limited to, acetaminophen, bupivacaine, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papavereturn, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

The therapeutic agent in the drug depot may include, but is not limited to, members of the fibroblast growth factor family, including acidic and basic fibroblast growth factor (FGF-1 and FGF-2) and FGF-4, members of the platelet-derived growth factor (PDGF) family, including PDGF-AB, PDGF-BB and PDGF-AA; EGFs; the TGF-β superfamily, including TGF-β1, 2 or 3; osteoid-inducing factor (OIF); angiogenin(s); endothelins; hepatocyte growth factor or keratinocyte growth factor; members of the bone morphogenetic proteins (BMP's) BMP-1, BMP-3, BMP-2; OP-1, BMP-2A, BMP-2B, or BMP-7; HBGF-1 or HBGF-2; growth differentiation factors (GDF's); members of the hedgehog family of proteins, including indian, sonic and desert hedgehog; ADMP-1; other members of the interleukin (IL) family; or members of the colony-stimulating factor (CSF) family, including CSF-1, G-CSF, and GM-CSF, or isoforms thereof; or VEGF, NELL-1 (neural epidermal growth factor-like 1), CD-RAP (cartilage-derived retinoic acid-sensitive protein) or combinations thereof.

In some embodiments, the drug depot comprises osteogenic proteins. Exemplary osteogenic proteins include, but are not limited to, OP-1, OP-2, OP-3, BMP-2, BMP-3, BMP-3b, BMP-4, BMP-5, BMP-6, BMP-9, BMP-10, BMP-11, BMP-12, BMP-13, BMP-14, BMP-15, GDF-1, GDF-2, GDF-3, GDF-5, GDF-6, GDF-7, GDF-8, GDF-9, GDF-10, GDF-11, GDF-12, CDMP-1, CDMP-2, CDMP-3, DPP, Vg-1, Vgr-1, 60A protein, NODAL, UNIVIN, SCREW, ADMP, NEURAL, and TGF-beta. As used herein, the terms "morphogen," "bone morphogen," "BMP," "osteogenic protein" and "osteogenic factor" embrace the class of proteins typified by human osteogenic protein 1 (hOP-1).

Exemplary growth factors include, but are not limited to, members of the transforming growth factor beta family, including bone morphogenetic protein 2 (BMP-2); bone morphogenetic protein 4 (BMP-4); and transforming growth factors beta-1, beta-2, and beta-3 (potent keratinocyte growth factors). Other useful members of the transforming growth factor beta family include BMP-3, BMP-5, BMP-6, BMP-9, DPP, Vgl, Vgr, 60A protein, GDF-1, GDF-3, GDF-5, GDF-6, GDF-7, CDMP-1, CDMP-2, CDMP-3, BMP-10, BMP-11, BMP-13, BMP-15, Univin, Nodal, Screw, ADMP, Neural, and amino acid sequence variants thereof. Other growth factors include epidermal growth factor (EGF), which induces proliferation of both mesodermal and ectodermal cells, particularly keratinocytes and fibroblasts; platelet-derived growth factor (PDGF), which exerts proliferative effects on mesenchymal cells; fibroblast growth factor (FGF), both acidic and basic; and insulin-like growth factor 1 (IGF-1) or 2 (IGF-2), which mediate the response to growth hormone, particularly in bone growth. Further growth factors include osteogenic proteins. A particularly preferred osteogenic protein is OP-1, also known as bone morphogenetic protein 7 (BMP-7). OP-1 is a member of the transforming growth factor beta gene superfamily.

The clonidine may also be administered with non-active ingredients. These non-active ingredients may have multi-functional purposes including the carrying, stabilizing and controlling the release of the therapeutic agent(s). The sustained release process, for example, may be by a solution-diffusion mechanism or it may be governed by an erosion-sustained process. Typically, the depot (e.g., fiber, strip, pellet, etc.) will be a solid or semi-solid formulation comprised of a biocompatible material that can be biodegradable.

In some embodiments, the implantable medical device comprises a drug depot. In various embodiments, a plurality of drug depots (e.g., pellets) can be administered to a surgical site.

In some embodiments, a plurality of drug depots are provided (e.g., in a kit) and administered to a surgical site and triangulate and/or surround the site to treat post-operative pain. In various embodiments, a plurality of drug depots comprise about 1, 2, 3, 4, 5, 6, 7, 8, 9 or 10 drug depots.

Exemplary excipients, plasticizers, and/or pore forming agents that may be formulated with clonidine in addition to the biodegradable polymer include but are not limited to MgO (e.g., 1 wt. %), mPEG, propylene glycol, mannitol, trehalose, TBO-Ac, Span-65, Span-85, pluronic F127, sorbitol, cyclodextrin, maltodextrin, pluronic F68, CaCl, dextran, dextran sulphate, dextran phosphate, hydroxypropylcellulose, ethylcellulose, PEG 1500, PEG 400, PEG3350 or combinations thereof. In some embodiments, the excipients comprise from about 0.001 wt. % to about 50 wt. % of the formulation. In some embodiments, the excipients comprise from about 0.001 wt. % to about 40 wt. % of the formulation. In some embodiments, the excipients comprise from about 0.001 wt. % to about 30 wt. % of the formulation. In some embodiments, the excipients comprise from about 0.001 wt. % to about 20 wt. % of the formulation. In some embodiments, the excipients comprise from about 0.001 wt. % to about 10 wt. % of the formulation. In some embodiments, the excipients comprise from about 0.001 wt. % to about 50 wt. % of the formulation. In some embodiments, the excipients comprise from about 0.001 wt. % to about 2 wt. % of the formulation.

In some embodiments, the drug depot material may have a melting point or glass transition temperature close to or higher than body temperature, but lower than the decomposition or degradation temperature of the therapeutic agent. However, the predetermined erosion of the depot (e.g., drug depot) material can also be used to provide for slow release of the loaded therapeutic agent(s). Non-biodegradable polymers include but are not limited to PVC and polyurethane. In some embodiments, a plasticizer is used to lower glass translation temperature in order to affect stability of the drug depot.

In various embodiments, the drug depot comprises clonidine, bupivacaine or lidocaine and a biodegradable polymer in amorphous, crystalline or semicrystalline form; where the crystalline form may include polymorphs, solvates or hydrates.

In some embodiments, the clonidine can be in powdered form having a particle size predominantly in a range from about 3.5 to about 10 micrometers that can be reconstituted with the polymer for delivery.

In some embodiments, the drug depot has a modulus of elasticity in the range of about $1 \times 10^2$ to about $6 \times 10^5$ dyn/cm$^2$, or $2 \times 10^4$ to about $5 \times 10^5$ dyn/cm$^2$, or $5 \times 10^4$ to about $5 \times 10^5$ dyn/cm$^2$. In some embodiments, the drug depot is in the form of a solid. In some embodiments, the drug depot comprises clonidine, bupivacaine or lidocaine.

In some embodiments, the clonidine, bupivacaine, lidocaine, and/or GABA compound is administered in a drug depot that is solid or in semi-solid form. The solid or semi-solid form of the drug depot may have a pre-dosed viscosity in the range of about 1 to about 2000 centipoise (cps), 1 to about 200 cps, or 1 to about 100 cps. After the solid or semi-solid drug depot is administered to the target site, the viscosity of the semi-solid or solid drug depot will increase and the semi-solid will have a modulus of elasticity in the range of about $1 \times 10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In various embodiments, the semi-solid or solid drug depot may comprise a polymer having a molecular weight, as shown by the inherent viscosity, from about 0.10 dL/g to about 1.2 dL/g or from about 0.20 dL/g to about 0.50 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

In some embodiments, the drug depot may comprise an 8% loaded 60:40 LCL 5A with a 6.5% content having a 0.4 mm diameter; an 8% loaded 60:40 LCL 5A with a 6.6% content having a 0.8 mm diameter; or a 16% loaded 60:40 LCL 5A with a 13.2% content having a 0.6 mm diameter.

In some embodiments, the drug depot may not be fully biodegradable. For example, the drug depot may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics, methacrylates, poly(N-isopropylacrylamide), PEO-PPO-PEO (pluronics) or combinations thereof. Typically, these types of matrices may need to be removed after a certain amount of time.

In some instances, it may be desirable to avoid having to remove the drug depot after use. In those instances, the drug depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (e.g., fiber, strip, pellet, etc.) (homogeneous or bulk erosion).

In various embodiments, the depot (e.g., fiber, strip, pellet, etc.) may comprise a bioerodible, a bioabsorbable, and/or a biodegradable biopolymer that may provide immediate release, or sustained release of the clonidine. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), poly(orthoester)s (POE), poly(esteramide)s, polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof.

In some embodiments, the drug depot comprises biodegradable polymers comprising wherein the at least one biodegradable polymer comprises one or more of poly (lactide-co-glycolide) (PLGA), polylactide (PLA), polyglycolide (PGA), D-lactide, D,L-lactide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly(L-lactide-co-caprolactone), poly(D-lactide-co-caprolactone), poly(D,L-lactide), poly(D-lactide), poly(L-lactide), poly(esteramide) or a combination thereof.

Mannitol, trehalose, dextran, mPEG and/or PEG may be used as a plasticizer for polymer. These plasticizers impart malleability to the resulting formulations. In some embodiments, the polymer and/or plasticizer may also be coated on the drug depot to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the drug from the depot (e.g., fiber, strip, pellet, etc.). In some embodiments, the range of the coating on the drug depot ranges from about 5 microns to about 250 microns or 5 microns to about 200 microns to delay release from the drug depot.

In various embodiments, the drug depot comprises poly (lactide-co-glycolide) (PLGA), polylactide (PLA), polyglycolide (PGA), D-lactide, D,L-lactide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly(L-lactide-co-caprolactone), poly(D-lactide-co-caprolactone), poly(D,L-lactide), poly(D-lactide), poly(L-lactide), poly(esteramide) or a combination thereof and has an inherent viscosity of 0.2 to about 0.5 dl/gm or 0.6 to about 1.0 dL/gm and a MW of 30,000 to about 125,000 Da.

In some embodiments, the drug depot comprises one or more polymers (e.g., PLA, PLGA, etc.) having a MW of from about 15,000 to about 150,000 Da, from about 25,000 to about 100,000 Da or from about 30,000 to about 50,000 Da.

As persons of ordinary skill in the art are aware, in some embodiments, when implantable depot (e.g., fiber, strip, pellet, etc.) compositions having a blend of polymers with different end groups are used the resulting formulation will have a lower burst index and a regulated duration of delivery. For example, one may use polymers with acid (e.g., carboxylic acid) and ester end groups (e.g., methyl or ethyl ester end groups).

Additionally, by varying the comonomer ratio of the various monomers that form a polymer (e.g., the L/G (lactic acid/glycolic acid) or G/CL (glycolic acid/polycaprolactone) ratio for a given polymer) there will be a resulting depot (e.g., fiber, strip, pellet, etc.) composition having a regulated burst index and duration of delivery. For example, a depot (e.g., fiber, strip, pellet, etc.) composition having a polymer with a L/G ratio of 50:50 may have a short duration of delivery ranging from about two days to about one month; a depot (e.g., fiber, strip, pellet, etc.) composition having a polymer with a L/G ratio of 65:35 may have a duration of delivery of about two months; a depot (e.g., fiber, strip, pellet, etc.) composition having a polymer with a L/G ratio of 75:25 or L/CL ratio of 75:25 may have a duration of delivery of about three months to about four months; a depot (e.g., fiber, strip, pellet, etc.) composition having a polymer ratio with a L/G ratio of 85:15 may have a duration of delivery of about five months; a depot (e.g., fiber, strip, pellet, etc.) composition having a polymer with a L/CL ratio of 25:75 or PLA may have a duration of delivery greater than or equal to six months; a depot (e.g., fiber, strip, pellet, etc.) composition having a terpolymer of CL/G/L with G greater than 50% and L greater than 10% may have a duration of delivery of about one month and a depot (e.g., fiber, strip, pellet, etc.) composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot (e.g., fiber, strip, pellet, etc.) compositions having a blend of polymers having different molecular weights, end groups and comonomer ratios can be used to create a depot (e.g., fiber, strip, pellet, etc.) formulation having a lower initial burst and a regulated duration of delivery.

The depot (e.g., fiber, strip, pellet, etc.) may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. If the depot (e.g., fiber, strip, pellet, etc.) is to be placed in the spinal area, in various embodiments, the depot (e.g., fiber, strip, pellet, etc.) may comprise sterile preservative free material.

The depot (e.g., fiber) can be different sizes, shapes and configurations. There are several factors that can be taken into consideration in determining the size, shape and configuration of the drug depot. For example, both the size and shape may allow for ease in positioning the drug depot at the target tissue site that is selected as the implantation. In addition, the shape and size of the system should be selected so as to minimize or prevent the drug depot from moving after implantation. In various embodiments, the drug depot can be shaped like a rod or a flat surface such as a film or sheet (e.g., ribbon-like) or the like. Flexibility may be a consideration so as to facilitate placement of the drug depot.

In various embodiments, the drug depot can be different sizes, for example, the drug depot may be a length of from about 0.5 mm to 50 mm and have a diameter of from about 0.01 to about 4 mm. In various embodiments, as the diameter decreases, the surface area that comes in contact with the bodily fluid of the depot (e.g., fiber, strip, pellet, etc.) increases and therefore release of the drug from the depot (e.g., fiber, strip, pellet, etc.) increases. In various embodiments, the drug depot may have a layer thickness of from about 0.005 to 1.0 mm, such as, for example, from 0.05 to 0.75 mm. In various embodiments, the length of the drug depot is determined based on the length needed to treat the target tissue site.

Radiographic markers can be included on the drug depot to permit the user to position the depot (e.g., fiber, strip, pellet, etc.) accurately into the target site of the patient. These radiographic markers will also permit the user to track movement and degradation of the depot (e.g., fiber, strip, pellet, etc.) at the site over time. In this embodiment, the user may accurately position the depot (e.g., fiber, strip, pellet, etc.) in the site using any of the numerous diagnostic imaging procedures. Such diagnostic imaging procedures include, for example, X-ray imaging or fluoroscopy. Examples of such radiographic markers include, but are not limited to, barium, calcium phosphate, bismuth, iodine, tantalum, tungsten, and/or metal beads or particles. In various embodiments, the radiographic marker could be a spherical shape or a ring around the depot (e.g., fiber, strip, pellet, etc.).

In some embodiments, a drug depot is provided that controls delivery of therapeutic agents to local, target tissues and secures itself to a target tissue site. In some embodiments, the drug depot is a flexible, drug loaded pellet or strip or fiber. In some embodiments, the drug depot is flexible, biodegradable that is loaded with the drug and/or drug coated to provide sustained release of a therapeutic to a local tissue site. In some embodiments, drug release is in days to months. In some embodiments, the drug depot comprises polymers, such as, for example, 10:90 poly(D,L-lactide-co-caprolactone), 85:15 poly(D,L-lactide-co-caprolactone), or 60:40 poly(L,lactide-co-caprolactone). Degradation times for the polymers could be weeks to months. In some embodiments, drugs are used such as, for example, an analgesic, anti-inflammatory and/or steroids, which are coated on the drug depot or uniformly distributed throughout the drug depot.

In some embodiments, the drug depot comprises a plurality of pores. In some embodiments, at least 10% of the pores are between about 10 micrometers and about 500 micrometers at their widest points. In some embodiments, at least 20% of the pores are between about 50 micrometers and about 150 micrometers at their widest points. In some embodiments, at least 30% of the pores are between about 30 micrometers and about 70 micrometers at their widest points. In some embodiments, at least 50% of the pores are between about 10 micrometers and about 500 micrometers at their widest points. In some embodiments, at least 90% of the pores are between about 50 micrometers and about 150 micrometers at their widest points. In some embodiments, at least 95% of the pores are between about 100 micrometers and about 250 micrometers at their widest points. In some embodiments, 100% of the pores are between about 10 micrometers and about 300 micrometers at their widest points.

In some embodiments, the drug depot has a porosity of at least about 30%, at least about 50%, at least about 60%, at least about 70%, at least about 90%. The pore enhances release of the clonidine for treatment of chronic pain.

In some embodiments, the depot may comprise natural and/or synthetic material. For example, the drug depot may comprise poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters (POE), polyaspirins, polyphosphagenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, polyglycolide (PGA), D-lactide, D,L-lactide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly(L-lactide-co-caprolactone), poly(D-lactide-co-caprolactone), poly(D,L-lactide), poly(D-lactide), poly(L-lactide), poly(esteramide), dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyetheretherketone, polymethylmethacrylate, silicone, hyaluronic acid, chitosan, or combinations thereof.

In some embodiments, the depot has a thickness of from 0.25 mm to 5 mm, or from about 0.4 mm to about 2 mm, or 0.4 mm to about 1 mm. In some embodiments, the depot has a length of about 1 mm to about 300 mm or about 5 mm to 200 mm or about 5 mm to about 150 mm.

In some embodiments, the diameter of the depot can range from 0.1 mm to 10 mm. In some embodiments, the diameter of the drug depot can range from 0.1 mm to 5 mm, 0.1 mm to 3 mm or 0.1 mm to 1 mm.

In some embodiments, the depot may be made by injection molding, compression molding, blow molding, thermoforming, die pressing, slip casting, electrochemical machining, laser cutting, water-jet machining, electrophoretic deposition, powder injection molding, sand casting, shell mold casting, lost tissue scaffold casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof.

In some embodiments, a therapeutic agent (including one or more clonidine compounds) may be disposed on or in the depot by hand by soaking, electrospraying, ionization spraying or impregnating, vibratory dispersion (including sonication), nozzle spraying, compressed-air-assisted spraying, brushing and/or pouring.

In some embodiments, the depot may comprise sterile and/or preservative free material. The depot can be implanted by hand or machine in procedures such as for example, laparoscopic, arthroscopic, neuroendoscopic, endoscopic, rectoscopic procedures or the like. In some embodiments, the initial burst surfaces can be disposed on the edges of the depot so that upon contact with the target tissue site, the edges will begin to release the clonidine. In some embodiments, the body of the depot can comprise dense, entangled polymers and have the clonidine to provide slower release of the clonidine.

Alternatively, the clonidine can be disposed homogenously throughout the depot to provide continuous extended release of the clonidine. In some embodiments, the clonidine can be layered in the depot with some portions having different concentrations to provide burst release and then slower release of the clonidine in areas that have dense crosslinked polymers, such as for example, in the core of the drug depot.

The dosage of clonidine released from the depot may be from approximately 0.0005 to approximately 960 µg/day. Additional dosages of clonidine include from approximately 0.0005 to approximately 900 µg/day; approximately 0.0005 to approximately 500 µg/day g/day; approximately 0.0005 to approximately 250 µg/day; approximately 0.0005 to approximately 100 µg/day; approximately 0.0005 to approximately 75 µg/day; approximately 0.001 to approximately 70 µg/day; approximately 0.001 to approximately 65 µg/day; approximately 0.001 to approximately 60 µg/day; approximately 0.001 to approximately 55 µg/day; approximately 0.001 to approximately 50 µg/day; approximately 0.001 to approximately 45 µg/day; approximately 0.001 to approximately 40 µg/day; approximately 0.001 to approximately 35 µg/day; approximately 0.0025 to approximately 30 µg/day; approximately 0.0025 to approximately 25 µg/day; approximately 0.0025 to approximately 20 µg/day; approximately 0.0025 to approximately 15 µg/day; approximately 0.0025 to approximately 10 µg/day; approximately 0.0025 to approximately 5 µg/day; and approximately 0.0025 to approximately 2.5 µg/day. In another embodiment, the dosage of clonidine is from approximately 0.005 to approximately 15 µg/day. In another embodiment, the dosage of clonidine is from approximately 0.005 to approximately 10 µg/day. In another embodiment, the dosage of clonidine is from approximately 0.005 to approximately 5 .mu.g µg/day. In another embodiment, the dosage of clonidine is from approximately 0.005 to 2.5 µg/day. In some embodiments, the amount of clonidine is between 40 and 600 µg/day. In some embodiments, the amount of clonidine is between 200 and 400 µg/day.

In some embodiments, the therapeutically effective dosage amount (e.g., clonidine dose) and the release rate profile are sufficient to reduce inflammation and/or pain for a period of at least 14 days, for example, 14-90 days, 14-30 days, 14-60 days, 21-90 days, 21-180 days; 14-210 days, or 14 days to 6 months or 1 year or longer.

In some embodiments, the clonidine depot is designed for a bolus dose or burst dose within 1, 2, or 3 days after implantation to provide an immediate release of the clonidine for treatment of pain and/or inflammation.

In some embodiments, the depot has a modulus of elasticity in the range of about $1 \times 10^2$ to about $6 \times 10^5$ dynes/cm$^2$, or $2 \times 10^4$ to about $5 \times 10^5$ dynes/cm$^2$, or $5 \times 10^4$ dynes/cm$^2$ to about $5 \times 10^5$ dynes/cm$^2$.

In some embodiments, the semi-solid or solid depot 10 may comprise a polymer having a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

In some embodiments, the drug depot may have a burst release surface that releases about 10%, 15%, 20%, 25%, 30%, 35%, 45%, to about 50% of the clonidine over 24 or 48 hours.

In some embodiments, the depot comprises a polymer having an average molecular weight of the polymer can be from about 1000 to about 10,000,000 Da; or about 1,000 to about 1,000,000 Da; or about 5,000 Da to about 500,000 Da; or about 10,000 Da to about 100,000 Da; or about 20,000 Da to 50,000 Da.

In some embodiments, when the polymer materials have different chemistries (e.g., high MW DLG 5050 and low MW DL), the high MW polymer may degrade faster than the low MW polymer.

In some embodiments, the depot may comprise a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethyl-methacrylate), poly-(methoxyethylmethacrylate), poly(methoxyethoxyethylmethacrylate), polymethyl-methacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In some embodiments, the depot may comprise gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. In some embodiments, the drug depot may comprise polyvinyl alcohol, acrylamides such as polyacrylic acid and poly(acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof.

In various embodiments, rather than directly admixing the therapeutic agent into the depot, microspheres may be dispersed within the depot, the microspheres being loaded with clonidine. In one embodiment, the microspheres provide for a sustained release of the clonidine.

Microspheres, much like a fluid, may disperse relatively quickly, depending upon the surrounding tissue type, and hence disperse the clonidine. In some situations, this may be desirable; in others, it may be more desirable to keep the clonidine tightly constrained to a well-defined target site. The present disclosure also contemplates the use of adherent gel or adhesive to constrain the depot close to the target tissue site. In this embodiment, an adherent gel or adhesive is used to anchor the depot to the target tissue site. The adherent gel or adhesive can, like the depot, also have the therapeutic agent disposed within it. In this way, the depot and the adhesive release the therapeutic agent (e.g., clonidine, statin, etc.) at or near the target tissue site.

Drug Depot Delivery

It will be appreciated by those with skill in the art that the depot (e.g., fiber, pellet, etc.) can be administered to the target site using a "cannula" or "needle" that can be a part of a drug delivery device e.g., a syringe, a gun drug delivery device, or any medical device suitable for the application of a drug to a targeted organ or anatomic region. The cannula or needle of the device is designed to cause minimal physical and psychological trauma to the patient.

In some embodiments, the depot can be sutured to a target tissue site using a suturing needle. The dimensions of the needle, among other things, will depend on the site for implantation. For example, the width of the muscle planes in different surgical procedures can vary from 1-40 cm. Thus, the needle, in various embodiments, can be designed for these specific areas.

Needles may have different shapes such as for example half curved or ski shaped, ¼ circle, ⅜ circle, ½ circle, ⅝ circle, compound curve or the like. The thickness of the needle will also depend on the site of implantation. In various embodiments, the thickness includes, but is not limited to, from about 0.05 to about 1.655. The gauge of the needle may be the widest or smallest diameter or a diameter in between for insertion into a human or animal body. The widest diameter is typically about 14 gauge, while the smallest diameter is about 25 gauge. In various embodiments the gauge of the needle or cannula is about 18 to about 22 gauge.

In various embodiments, like the drug depot, the cannula or needle includes dose radiographic markers that indicate location at or near the site beneath the skin, so that the user may accurately position the depot (e.g., fiber) at or near the site using any of the numerous diagnostic imaging procedures. Such diagnostic imaging procedures include, for example, X-ray imaging or fluoroscopy. Examples of such radiographic markers include, but are not limited to, barium, bismuth, tantalum, tungsten, iodine, calcium, and/or metal beads or particles.

In various embodiments, the needle or cannula may include a transparent or translucent portion that can be visualizable by ultrasound, fluoroscopy, X-ray, or other imaging techniques. In such embodiments, the transparent or translucent portion may include a radiopaque material or ultrasound responsive topography that increases the contrast of the needle or cannula relative to the absence of the material or topography.

The drug depot may be sterilizable. In various embodiments, one or more components of the drug depot are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot (e.g., fiber) and/or one or more components of the device, including, but not limited to, gas sterilization, such as, for example, with ethylene oxide or steam sterilization.

In various embodiments, a kit is provided that may include additional parts along with the drug depot combined together to be used to implant the drug depot. The kit may include the drug depot device in a first compartment. The second compartment may include a canister holding the drug depot and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. A fifth compartment may include an agent for radiographic imaging. Each tool may be separately packaged in a plastic pouch that is radiation sterilized. A cover of the kit may include illustrations of the implanting procedure and a clear plastic cover may be placed over the compartments to maintain sterility. In some embodiments, a kit is provided with instruction to use an injectable drug from another kit.

In various embodiments, a method for delivering a therapeutic agent into a site of a patient is provided, the method comprising inserting a needle at or near a target tissue site and suturing the drug depot at the target site beneath the skin of the patient. In this way unwanted migration of the drug depot away from the target site is reduced or eliminated.

In some embodiments, the drug depot can be delivered to any site beneath the skin, including, but not limited to, at least one muscle, ligament, tendon, cartilage, spinal disc, spinal foraminal space, near the spinal nerve root, connective tissue, fascia, subcutaneous space, or spinal canal.

In some embodiments, it is preferable to co-administer clonidine with an antagonist to counteract undesirable effects, for example the blood pressure decrease that can be caused by clonidine. Exemplary antagonists include but are not limited to phentolamine, yohimbine, tolazoline and piperoxane. Additionally, compounds such as 5-fluorodeoxyuridine (FUDR) and 3,4 dehydroprolene may also be included. These compounds may prevent or reduce glial and fibroblastic scar formation associated with some types of surgeries.

Another embodiment is directed to a method for treating a mammal suffering from pain, said method comprising administering a therapeutically effective amount of clonidine at a target site beneath the skin. The clonidine (or pharmaceutically acceptable salt) may for example be administered locally to the target tissue site disposed within or on a drug depot.

In some embodiments, the clonidine is encapsulated in a plurality of matrices comprising microparticles, microspheres, microcapsules, and/or microfibers and then put into a drug depot.

In some embodiments there is a method for making an implantable drug depot. The method may comprise combining a biocompatible polymer and a therapeutically effective amount of clonidine or a pharmaceutically acceptable salt thereof and forming the implantable drug depot from the combination.

Method of Making the Depot

In various embodiments, the drug depot comprising the clonidine can be made by combining a biocompatible polymer and a therapeutically effective amount of clonidine or pharmaceutically acceptable salt thereof and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot (e.g., fiber, pellet, strip, etc.) to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: clonidine and other therapeutic agent(s) and other optional additives such as radiographic agent(s), etc. in dissolved or dispersed form. This results in a polymeric drug depot region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot (e.g., fiber, pellet, strip, etc.) or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: clonidine, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, clonidine may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the clonidine containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot (e.g., fiber) is formed comprising PLGA or PLA polymer, a radio-opacifying agent (e.g., bismuth subcarbonate), and a therapeutic agent prone to degradation by heat and/or mechanical shear (e.g., clonidine), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of clonidine because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot (e.g., fiber. Pellet, strip, etc.) is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion process may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric drug depot layers or regions that have permeability to fluids to allow immediate and/or sustained drug release). Multi-region depots (e.g., fibers, pellet, strip, etc.) can also be formed by other processing and shaping techniques such as co-injection or sequential injection molding technology.

In various embodiments, the depot (e.g., fiber, pellet, strip, etc.) that may emerge from the thermoplastic processing (e.g., pellet) is cooled. Examples of cooling processes include air cooling and/or immersion in a cooling bath. In some embodiments, a water bath is used to cool the extruded depot (e.g., fiber, pellet, strip, etc.). However, where a water-soluble therapeutic agent such as clonidine is used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot (e.g., fiber) surface, thus controlling or minimizing a high drug dose "initial burst" or "bolus dose" upon implantation or insertion if this is release profile is not desired.

In various embodiments, the drug depot can be prepared by mixing or spraying the drug with the polymer and then molding the depot (e.g., fiber) to the desired shape. In various embodiments, clonidine is used and mixed or sprayed with the PLGA or PEG550 polymer, and the resulting depot (e.g., fiber) may be formed by extrusion and dried.

In various embodiments, there is a pharmaceutical formulation comprising: clonidine, wherein the clonidine comprises from about 0.1 wt. % to about 40 wt. % of the formulation, and at least one biodegradable polymer. In some embodiments, the clonidine comprises from about 3 wt. % to about 20 wt. %, about 3 wt. % to about 18 wt. %, about 5 wt. % to about 15 wt. %, 0.1 wt % to about 10 wt %, about 0.1 wt % to about 3 wt %, or about 7.5 wt. % to about 12.5 wt. % of the formulation. By way of example, when using a 5%-15% clonidine composition, the mole ratio of clonidine to polymer would be from approximately 16-53 when using an approximately 80 kDalton polymer that has a 267 grams/mole ratio. By way of another example, when using a 5%-15% clonidine base in the composition, the mole ratio of clonidine base to polymer would be from approximately 18-61 with a mole mass of 230 g/mol.

In some embodiments, the clonidine can be in the formulation in an amount of about 1%, 5%, 10%, 15%, 20%, 25%, 30%, 35%, or 40% by weight based on the total weight of the formulation.

In some embodiments, the drug depot comprises at least one biodegradable material in a wt % of about 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 76%, 75%, 74%, 73%, 72%, 71%, 70%, 65%, 60%, 55%, 50%, 45%, 35%, 25%, 20%, 15%, 10%, or 5% based on the total weight of the depot (e.g., fiber) and the remainder is active and/or inactive pharmaceutical ingredients.

In some embodiments, the at least one biodegradable polymer comprises poly(lactic-co-glycolide) (PLGA) or poly(orthoester) (POE) or a combination thereof. The poly (lactic-co-glycolide) may comprise a mixture of polyglycolide (PGA) and polylactide and in some embodiments, in the mixture, there is more polylactide than polyglycolide. In various embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer is polyglycolide.

In various embodiments, the drug particle size (e.g., clonidine) is from about 5 to 30 micrometers, or about 2 microns to about 20 microns, or from 30 microns to 100 microns, however, in various embodiments ranges from about 1 micron to 250 microns may be used. In some embodiments, the biodegradable polymer comprises at least 50 wt. %, at least 60 wt. %, at least 70 wt. %, at least 80 wt. % of the formulation, at least 85 wt. % of the formulation, at least 90 wt. % of the formulation, at least 95 wt. % of the formulation or at least 97 wt. % of the formulation. In some embodiments, the at least one biodegradable polymer and the clonidine are the only components of the pharmaceutical formulation.

In some embodiments, at least 75% of the particles have a size from about 10 micrometer to about 200 micrometers. In some embodiments, at least 85% of the particles have a size from about 10 micrometer to about 200 micrometers. In some embodiments, at least 95% of the particles have a size from about 10 micrometer to about 200 micrometers. In some embodiments, all of the particles have a size from about 10 micrometer to about 200 micrometers.

In some embodiments, at least 75% of the particles have a size from about 20 micrometer to about 180 micrometers. In some embodiments, at least 85% of the particles have a size from about 20 micrometers to about 180 micrometers. In some embodiments, at least 95% of the particles have a size from about 20 micrometer to about 180 micrometers. In some embodiments, all of the particles have a size from about 20 micrometer to about 180 micrometers. In some embodiments, at least 80% of the particles have a size from 5 microns to about 100 microns on a volume basis.

In some embodiments, at least 75% of the particles have a size from about 0.5 micrometer to about 100 micrometers. In some embodiments, at least 85% of the particles have a size from about 0.5 micrometers to about 100 micrometers. In some embodiments, at least 95% of the particles have a size from about 0.5 micrometer to about 100 micrometers. In some embodiments, all of the particles have a size from about 0.5 micrometer to about 100 micrometers. In some embodiments, at least 80% of the particles have a size from 2 microns to about 50 microns on a volume basis.

In some embodiments, there is a pharmaceutical formulation comprising: clonidine, wherein the clonidine is in the form of a hydrochloride salt, and comprises from about 0.1 wt. % to about 30 wt. % of the formulation, and at least one biodegradable polymer, wherein the at least one biodegradable polymer comprises poly(lactide-co-glycolide) (or poly(lactic-co-glycolic acid)) or poly(orthoester) or a combination thereof, and said at least one biodegradable polymer comprises at least 70 wt. % of said formulation.

In some embodiments, the drug depot comprises about 95 wt % poly(D,L-lactide) and 5 wt % clonidine HCl where the polymer has an ester end group and 50,000-70,000 Da MW and an IV 0.45-0.55 dL/g and has a burst release of under 10% of the amount of drug in the depot (e.g., fiber, pellet, strip, etc.) within 24 hours (e.g., 5-10 wt %) or 2-40 mcg in 24 hours. This formulation has 50% of total cumulative dose remaining for at least 60 days. About 80% of the particles in this depot (e.g., fiber) including the clonidine are from about 5 to about 150 microns or 5-100 microns. The depot (e.g., fiber) releases about 0.5 mcg/day up to about 5 mcg/day of clonidine in 24 hours and then continues release for 70 days.

In some embodiments, the drug depot comprises about 92 wt % poly(D,L-lactide) and 8 wt % clonidine HCl where the polymer has an ester end group and the polymer comprises 50,000-70,000 Da MW and an IV of about 0.45-0.55 dL/g and has a burst release of under 10% of the amount of drug in the depot (e.g., fiber) within 24 hours (e.g., 5-10%) or 5-6 mcg in 24 hours and then 1 to 20 mcg/day with a constant release for about 50 days, and then about 0.1 mcg to about 10 mcg/day for 70 days. This formulation has 50% of total cumulative dose remaining for at least 30-42 days and less than 80% cumulative drug release by 70 days. About 80% of the particles in this depot (e.g., fiber) including the clonidine are from about 5 to about 150 microns or 5-100 microns.

In some embodiments, the drug depot comprises about 85 wt % poly(D,L-lactide) and 15 wt % clonidine HCl where the polymer has an ester end group and the polymer comprises 50,000-70,000 Da MW and an IV of about 0.45-0.55 dL/g and has a burst release of under 10% of the amount of drug in the depot (e.g., fiber) within 24 hours (e.g., 5-10%) or 20-150 mcg in 24 hours and then 5 to 80 mcg/day with a constant release for about 30 days, and then about 0.1 mcg to about 5 mcg/day for 70 days. This formulation has about 80% of total cumulative dose released within 35 days and 20% over several months. About 80% of the particles in this depot (e.g., fiber) including the clonidine are from about 5 to about 150 microns or 5-100 microns.

In some embodiments, there is a pharmaceutical formulation comprising clonidine, wherein the clonidine is in a mixture of clonidine hydrochloride and clonidine base and the mixture comprises from about 0.1 wt. % to about 30 wt. % of the formulation and a polymer comprises at least 70% of the formulation. In some embodiments, the polymer in this formulation is polyorthoester.

In some embodiments, the formulation comprises a drug depot that comprises a biodegradable polyorthoester. The mechanism of the degradation process of the polyorthoester can be hydrolytical or enzymatical in nature, or both. In various embodiments, the degradation can occur either at the surface of the drug depot (heterogeneous or surface erosion) or uniformly throughout the drug delivery system depot (e.g., fiber) (homogeneous or bulk erosion). Polyorthoester can be obtained from A.P. Pharma, Inc. (Redwood City, Calif.) or through the reaction of a bis(ketene acetal) such as 3,9-diethylidene-2,4,8,10-tetraoxospiro[5,5]undecane (DETOSU) with suitable combinations of diol(s) and/or polyol(s) such as 1,4-trans-cyclohexanedimethanol and 1,6-hexanediol or by any other chemical reaction that produces a polymer comprising orthoester moieties.

In some embodiments, there are methods for treating acute pain. These methods comprise: administering a pharmaceutical composition to an organism, wherein said pharmaceutical composition (e.g., clonidine) comprises from about 0.1 wt. % to about 30 wt. % of the formulation, and at least one biodegradable polymer. In some embodiments, the loading is from about 0.1 wt % to about 10 wt %, about 0.1 wt % to about 3 wt %, 1 wt % to about 25 wt %, or about 5 wt. % to about 10 wt. %. In some embodiments, the loading is from about 10 wt. % to about 20 wt. %.

In some embodiment there is a higher loading of clonidine, e.g., at least 20 wt. %, at least 30 wt. %, at least 40 wt. %, at least 50 wt. %, at least 60 wt. %, at least 70 wt. %, at least 80 wt. %, or at least 90 wt. %.

A strategy of triangulation may be effective when administering these pharmaceutical formulations. Thus, a plurality (at least two, at least three, at least four, at least five, at least six, at least seven, etc.) drug depots comprising the pharmaceutical formulations may be placed around the target tissue site (also known as the pain generator or pain generation site) such that the target tissue site falls within a region that is either between the formulations when there are two, or within an area whose perimeter is defined by a set of plurality of formulations.

In some embodiments, when the drug depot is in pellet form and comprises 5%, 8% or 15% clonidine HCL to provide pain relief for chronic conditions (e.g., sciatica) for more than 30 days, one drug depot may not be enough. Therefore, in this embodiment, 1, 2, 3, 4, 5, 6, 7, 8, 9 or 10 pellets may be used to provide sufficient pain relief. These 1-10 drug depots/pellets can be triangulated around the pain generator to provide pain relief.

In some embodiments, the formulations are slightly rigid with varying length, widths, diameters, etc. For example, certain formulations may have a diameter of 0.50 mm and a length of 4 mm. It should be noted that particle size may be altered by techniques such as mort and pestle, jet-drying or jet milling.

In some embodiments, clonidine is released at a rate of 2-3 µg per day for a period of at least three days. In some embodiments, this release rate continues for, at least ten days, at least fifteen days, at least twenty-five days, at least fifty days, at least ninety days, at least one hundred days, at least one-hundred and thirty-five days, at least one-hundred and fifty days, or at least one hundred and eighty days. For some embodiments, 300-425 micrograms of clonidine as formulated with a biopolymer are implanted into a person at or near a target tissue site. If clonidine is implanted at multiple sites that triangulate the target site then in some embodiments, the total amount of clonidine at each site is a fraction of the total 300-425 micrograms. For example, one may implant a single dose of 324 micrograms at one site, or two separate doses of 162 micrograms at two sites, or three separate dose of 108 micrograms at three sites that triangulate the tissue site. It is important to limit the total dosage to an amount less than that which would be harmful to the organism. However, in some embodiments, although when there are a plurality of sites each site may contain less than the total dose that might have been administered in a single application, it is important to remember that each site will independent have a release profile, and the biopolymers' concentration and substance should be adjusted accordingly to ensure that the sustain release occurs over sufficient time.

In some embodiments, clonidine is released at a rate of 7-20 µg per day for a period of at least three days. In some embodiments, this release rate continues for, at least ten days, at least fifteen days, at least twenty-five days, at least fifty days, at least ninety days, at least one hundred days, at least one-hundred and thirty-five days, at least one-hundred and fifty days, or at least one hundred and eighty days. For some embodiments, 900-1050 micrograms of clonidine as formulated with a biopolymer are implanted into a person at or near a target tissue site. If clonidine is implanted at multiple sites that triangulate the target site then in some embodiments, the total amount of clonidine at each site is a fraction of the total 900-1050 micrograms. For example, one may implant a single dose of 975 micrograms at one site, or two separate doses of 650 micrograms at two sites, or three separate dose of 325 micrograms at three sites that triangulate the tissue site. It is important to limit the total dosage to an amount less than that which would be harmful to the organism. However, in some embodiments, although when there are a plurality of sites each site may contain less than the total dose that might have been administered in a single application, it is important to remember that each site will independent have a release profile, and the biopolymers' concentration and substance should be adjusted accordingly to ensure that the sustain release occurs over sufficient time.

The dosage of clonidine may be from approximately 0.0005 to approximately 960 µg/day. Additional dosages of clonidine include from approximately 0.0005 to approximately 900 µg/day; approximately 0.0005 to approximately 500 µg/day; approximately 0.0005 to approximately 250 µg/day; approximately 0.0005 to approximately 100 µg/day; approximately 0.0005 to approximately 75 µg/day; approximately 0.001 to approximately 70 µg/day; approximately 0.001 to approximately 65 µg/day; approximately 0.001 to approximately 60 µg/day; approximately 0.001 to approximately 55 µg/day; approximately 0.001 to approximately 50 µg/day; approximately 0.001 to approximately 45 µg/day; approximately 0.001 to approximately 40 µg/day; approximately 0.001 to approximately 35 µg/day; approximately 0.0025 to approximately 30 µg/day; approximately 0.0025 to approximately 25 µg/day; approximately 0.0025 to approximately 20 µg/day; approximately 0.0025 to approximately 15 µg/day; approximately 0.0025 to approximately 10 µg/day; approximately 0.0025 to approximately 5 µg/day; and approximately 0.0025 to approximately 2.5 µg/day. In another embodiment, the dosage of clonidine is from approximately 0.005 to approximately 15 µg/day. In another embodiment, the dosage of clonidine is from approximately 0.005 to approximately 10 µg/day. In another embodiment, the dosage of clonidine is from approximately 0.005 to approximately 5 µg/day. In another embodiment, the dosage of clonidine is from approximately 0.005 to 2.5 µg/day. In some embodiments, the amount of clonidine is between 40 and 600 µg/day. In some embodiments, the amount of clonidine is between 200 and 400 µg/day.

In some embodiments, the therapeutically effective dosage amount (e.g., clonidine dose) and the release rate profile are sufficient to reduce inflammation and/or pain for a period of at least one day, for example, 1-90 days, 1-10 days, 1-3 days, 3-7 days, 3-12 days; 3-14 days, 7-10 days, 7-14 days, 7-21 days, 7-30 days, 7-50 days, 7-90 days, 7-140 days, 14-140 days, 3 days to 135 days, 3 days to 180 days, or 3 days to 6 months or 1 year or longer.

In some embodiments the clonidine in the drug depot is designed for a bolus dose or burst dose within 1, 2, or 3 days after implantation to provide an immediate release of the clonidine for treatment of pain and/or inflammation.

In some embodiments, the clonidine drug depot is administered parenterally, e.g., by injection. In some embodiments, the injection is intrathecal, which refers to an injection into the spinal canal (intrathecal space surrounding the spinal cord). An injection may also be into a muscle or other tissue. In other embodiments, the clonidine depot (e.g., fiber) is administered by placement into an open patient cavity during surgery.

In some embodiments, the drug depot (i) comprises one or more immediate release layer(s) that is capable of releasing about 5% to about 20% of the clonidine or pharmaceutically acceptable salts thereof relative to a total amount of the clonidine or pharmaceutically acceptable salt thereof loaded in the drug depot (e.g., fiber) over a first period of up to 48 hours and (ii) one or more sustain release layer(s) that is capable of releasing about 21% to about 99% of the clonidine or pharmaceutically acceptable salt thereof relative to a total amount of the clonidine or pharmaceutically acceptable salt thereof loaded in the drug depot (e.g., fiber) over a subsequent period of up to 3 days to 90 days, 150 days, 180 days, or 6 months to 1 year.

In some embodiments, there is a drug depot (e.g., fiber) comprising clonidine or clonidine hydrochloride and a polymer, wherein the polymer is one more of various embodiments, the drug depot (e.g., fiber) comprises poly(lactide-co-glycolide) (PLGA), polylactide (PLA), polyglycolide (PGA), D-lactide, D,L-lactide, L-lactide, D,L-lactide-co-ϵ-caprolactone, D,L-lactide-co-glycolide-co-ϵ-caprolactone or a combination thereof.

In some embodiments, the polymer drug depot of the present application enables one to provide efficacy of the active ingredient that is equivalent to subcutaneous injections that deliver more than 2.5 times as much drug.

In some embodiments, the drug depot comprises a polymer having 65 mol. % poly L-lactide and 35 mol. % caprolactone, where the poly (L-lactide-co-caprolactone) has a MW of 30,000 to 40,000 Da and an IV of about 0.5-0.6 dL/g and has a burst release of under 35% of the amount of drug in the depot (e.g., fiber) within 24 hours (e.g., 5-15% within 4 hours). The drug depot comprises clonidine in an amount of 3-8 wt. %. The drug depot releases 400 mcg to about 1000 mcg for 7 days, which is about 40 mcg/day. This drug depot contains 5-10 wt % mannitol as an excipient. The clonidine has a particle size of 25 microns or less and a 90% volume diameter less than 50 microns. The degradation time in the body is not more than 8 months and the drug depot releases all of the clonidine within 2-4 weeks.

In some embodiments, the drug depot comprises a polymer having 10 mol. % poly D-L-lactide and 90 mol. % caprolactone, where the poly(D,L-lactide-co-caprolactone) has a MW of 50,000 to 125,000 Da and an IV of about 0.6 dL/g and has a burst release of under 25% of the amount of drug in the drug depot within 24 hours (e.g., 5-15% within 4 hours). The drug depot comprises clonidine in an amount of 3-10 wt. %. The drug depot releases 400 mcg to about 1000 mcg for 7 days, which is about 40 mcg/day. This drug depot contains from about 1% to about 5% by weight of mannitol or trehalose as a pore forming agent or plasticizer. The clonidine has a particle size of 5 microns or less and a 90% volume diameter less than 20 microns. The degradation time in the body is not more than 12 months and the drug depot (e.g., fiber) releases all of the clonidine within 2-4 weeks. As you drop the drug load the drug released from the depot (e.g., fiber) is faster.

The inherent viscosity (IV) designations for the polymers are mentioned in Table A below. In some embodiments, the polymers can have the following inherent viscosities.

TABLE A

| IV Target Designator | IV Range |
|---|---|
| 1 | 0.05-0.15 |
| 1.5 | 0.10-0.20 |
| 2 | 0.15-0.25 |
| 2.5 | 0.20-0.30 |
| 3 | 0.25-0.35 |
| 3.5 | 0.30-0.40 |
| 4 | 0.35-0.45 |
| 4.5 | 0.40-0.50 |
| 5 | 0.45-0.55 |
| 6 | 0.50-0.70 |
| 7 | 0.60-0.80 |
| 8 | 0.70-0.90 |
| 9 | 0.80-1.0 |
| 10 | 1.0-1.2 |

The final letter within the code of the polymer is the end group designator. For examples "E" refers to an ester end group, while "A" refers to an acid end group.

By way of example, 100 LCL 5A is a polymer that has an inherent viscosity of about 0.45-0.55 dL/g. It contains 100% poly(L-lactide-co-caprolactone), where the ratio of L-lactide to caprolactone is 60:40 and has an ester end group. It is available from Lakeshore Biomaterials, Birmingham, Ala.

EXAMPLES

The examples below with respect to certain formulations comprising clonidine as the biologically active agent show certain particularly advantageous results.

Example 1

Poly(D,L-lactide) [PLA] has been used in a variety of implantable, bio-degradable controlled release drug products. However, the local effects of a PLA drug product on nervous tissue has not been specifically studied. Clonidine, an α-2 adrenergic receptor agonist, has been shown to have local analgesic effects and is approved as an epidural analgesic to augment morphine therapy for intractable cancer pain. Investigational PLA pellet implants (4 mm×0.7 mm cylinders) containing up to 15% (w:w) clonidine HCL (CP) have been developed for the treatment of radicular back pain. This indication requires a careful investigation of the effects of the implants on nerve structure and function. Our central research question was to determine what would limit the dose of CP: systemic effects of the API or local adverse effects on nerve function or morphology.

Nerve local tolerance studies/systemic toxicity studies were conducted in both rats and goats. In the rodent model, pellets were surgically placed in a single pocket adjacent to the right sciatic nerve, mid-thigh. For the caprine model, pellets were delivered into the epidural space using an 18 gauge spinal needle under fluoroscopic guidance (targeting the most caudal interlumbar spinal nerve on the left side). Three different potencies of CP were created: 5% (CP-05), 8% (CP-08), and 15% (CP-15) clonidine HCL in PLA. Placebo pellets (PP) not containing clonidine were also tested.

In the rodent model, ≥2850 ug of clonidine HCL in the form of CP-08 (15 pellets) or CP 15 (9 or more pellets) were associated with systemic toxicity in the absence of adverse effects on nerve histology or function. The highest doses tested (4000 ug clonidine HCL in 12×CP-15) resulted in the death (found dead or termination in moribund condition) of 25% of females and 0% of males and non-lethal effects, some considered adverse, in the majority of surviving animals, with no adverse changes in the targeted sciatic nerve and no sensory or motor dysfunction. In the caprine model, neither systemic toxicity nor loss of nerve function was documented at any dose (up to the maximally achievable dose [6000 ug, 15×CP-15] limited by anatomical constraints around the target spinal nerve within the bony lateral foramen). Microscopic evaluation revealed no dose-response effects on nerve morphology, although mechanical damage to spinal nerves in cases where the pellets skewered the spinal nerves. Such mechanical damage to spinal nerve only occurred with a lateral needle approach to the foramen (transformational) and not with a dorsal approach (interlaminar). In conclusion, neither CP nor PP caused local toxic effects on nerve and it was determined that dosing of CP is likely to be limited by systemic effects of clonidine HCL.

Introduction

Poly(D,L) lactic acid (PLA) is a biodegradable polyester that been used as an encapsulating agent in several investigational sustained-release drug products. Weiniger C F, Golovanevski L, Domb A J, Ickowicz D: *Extended release formulations for local anaesthetic agents*, Anaesthesia 2012, 67:906-916. Drugs can be incorporated into PLA particles via mixing and melt extrusion. The drug can then diffuse through the polymer matrix and into the surrounding tissue in vivo. PLA is listed in the FDA database of Inactive Ingredients for Approved Drug Products as a periodontal drug delivery system and excipient for intramuscular injection and has been shown to be generally biocompatible, eliciting a mild, macrophage-driven foreign body response. Vogt F, Stein A, Rettemeier G, Krott N, Hoffmann R, vom Dahl J, Bosserhoff A K, Michaeli W, Hanrath P, Weber C, Blindt R: *Long-term assessment of a novel biodegradable paclitaxel-eluting coronary polylactide stent*, Eur Heart J 2004, 25:1330-1340. A PLA-based leuprolide acetate (GnRH analague) depot, Lupron®, is currently approved for intramuscular injection. However, the effects of PLA on the function and microscopic morphology of nerve tissue has not been adequately studied.

Clonidine, an α-2 adrenergic receptor agonist, was first approved by the FDA as an antihypertensive agent in 1974. In 1996, clonidine was approved as an epidural analgesic for the treatment of intractable cancer pain. More recently, clonidine has been shown to have local analgesic effects independent of effects on the central nervous system. Iskandar H, Benard A, Ruel-Raymond J, Cochard G, Manaud B: *The analgesic effect of interscalene block using clonidine as an analgesic for shoulder arthroscopy*, Anesth Analg 2003, 96:260-262, table of contents. Intra-articular administration of 150 mcg of clonidine HCL has been shown to be as effective as morphine in relieving post-surgical knee pain. Gentili M, Enel D, Szymskiewicz O, Mansour F, Bonnet F: *Postoperative analgesia by intraarticular clonidine and neostigmine in patients undergoing knee arthroscopy*, Reg Anesth Pain Med 2001, 26:342-347; Gentili M, Houssel P, Osman M, Henel D, Juhel A, Bonnet F: *Intra-articular morphine and clonidine produce comparable analgesia but the combination is not more effective*, Br J Anaesth 1997, 79:660-661. There is increasing evidence that these local analgesic effects may be mediated, in part, by anti-inflammatory actions of clonidine. Romero-Sandoval A, Bynum T, Eisenach J C: *Analgesia induced by perineural clonidine is enhanced in persistent neuritis*, Neuroreport 2007, 18:67-71; Romero-Sandoval A, Eisenach J C: *Clonidine reduces hypersensitivity and alters the balance of pro-and anti-inflammatory leukocytes after local injection at the site of inflammatory neuritis*, Brain Behav Immun 2007, 21:569-580; Kim M H, Hahn T H: *The effect of clonidine pretreatment on the perioperative proinflammatory cytokines, cortisol, and ACTH responses in patients undergoing total abdominal hysterectomy*, Anesth Analg 2000, 90:1441-1444.

In an attempt to leverage the analgesic and purported anti-inflammatory effects of clonidine to treat pain related to lumbar disk herniation, clonidine was formulated into PLA pellets sized to fit in the lumen of an 18 gauge spinal needle. Clonidine Pellets (CP) contain from 5 to 15% (w/w) clonidine HCL mixed with a poly (D,L) lactide polymer base, melt extruded and cut into 4 mm long×0.7 mm wide cylindrical pellets. A single CP appears to have sustained antinociceptive effects in the rat sciatic nerve chronic constriction model (unpublished researched, in review). In the proposed clinical indication, pellets will be delivered to the epidural space adjacent to spinal nerve/nerve roots affected by a lumbar disk herniation. The target indication necessitates an assessment of the local tolerance of nerve tissue to CP. To this end, the effects of the PLA pellets, with and without clonidine HCL, was studied following perineural placement in rats and goats.

Methods

Test Article

Clonidine HCL was obtained from Societa' Italiana Medicinali Scandiccini (SIMS, Reggelllo, Italy) and milled by Micron Technologies (Malvern, Pa.) prior to incorporation into PLA. The micronized clonidine HCL was mixed with poly(D,L-lactide) [CAS #26680-10-4] at 3 different concentrations (by weight): 5% (CP-05), 8% (CP-08), and 15% (CP-15) and extruded to a fiber that was then cut into 4 mm long×0.7 mm diameter pellets. Placebo PLA pellets not containing clonidine were also manufactured using the same methods.

Rodent Nerve Tolerance and Systemic Toxicity Model

Sprague Dawley rats (n=384 male and 384 female) were obtained from Charles River, Inc. Animals were divided into treatment groups as follows (with Groups 4-11 in order of increasing dose of active drug):

Group 1) Sham control
Group 2) 12× Placebo pellet (control for high dose CP-15)
Group 3) 15× Placebo pellet (control for high dose CP-05 and CP-08)
Group 4) 3×CP-08 pellets (total drug load ~570 mcg clonidine HCL)
Group 5) 3×CP-15 pellets (1000 mcg clonidine HCL)
Group 6) 6×CP-08 pellets (1140 mcg clonidine HCL)
Group 7) 15×CP-05 pellets (1830 mcg clonidine HCL)
Group 8) 6×CP-15 pellets (2000 mcg clonidine HCL)
Group 9) 15×CP-08 pellets (2850 mcg clonidine HCL)
Group 10) 9×CP-15 pellets (3000 mcg clonidine HCL)
Group 11) 12×CP-15 pellets (4000 mcg clonidine HCL)

Treatment groups 2-11 each included 32 male rats and 32 female rats. The sham group included 64 male rats and 64 female rats.

The PLA pellets were surgically implanted in a single intermuscular pocket adjacent to the right sciatic nerve. Sham animals underwent the same procedure, exposing the sciatic nerve without pellet implantation. Animals were anesthetized using 1-3% isoflurane delivered via a nose cone. The lateral aspect of the right hind leg was shaved from the stifle (femortibial) joint up to the hip (gluteal region). A skin incision was made on the upper thigh (proximal to stifle). Using blunt dissection, the femoral biceps and quadriceps muscles were separated to create an intermuscular pocket exposing the sciatic nerve. Test article was placed into the pocket adjacent to the nerve (and potentially in contact with the nerve). The pocket was closed by suturing the femoral biceps to the quadriceps using 5/0 absorbale suture material. An incisional splash block of bupivacaine solution (2 mg/kg) was performed prior to closing the skin incision with continuous subcuticular 5/0 absorbable sutures. The superficial margins of the incision were further secured with 2-Octyl cyanoacrylate liquid adhesive (Dermabond™). Subcutaneous injections of buprenophine (0.03 mg/kg) was provided to sham and placebo animal immediately post operatively and the day after surgery, if needed. Buprenphine was deemed unnecessary for animals treated with clonidine test article. Once animals regained sternal recumbancy, they were returned to their home cages.

Clinical observations were recorded at least daily throughout the study. Food consumption and bodyweight were assessed on a weekly basis. Subsets of animals (8 males and 8 females per group) were euthanized at 1, 6, 12, and 24 weeks post-operatively for histopathological assessments.

Based on the results of pilot studies, 15 pellets was considered to be the maximum technically achievable dose within the confines of para-sciatic test article placement. Higher pellet loads were more likely to migrate out of the intermuscular pockets, sometimes into the subcutaneous space. This migration away from the sciatic nerve would confound our interpretation of the nerve tissue local tolerance dose-response relationship. Fifteen pellets was reasonably contained adjacent to the sciatic nerve, and therefore was selected as the high dose for CP-05 and CP-08. The dose of CP-15, however, was limited by systemic toxicity rather than anatomical limitations. Based on pilot work, it was determined that 12 CP-15 pellets would be sufficient to establish a NOAEL and that 15 CP-15 pellets may cause excessive moribundity and fatalities (interfering with sub-acute and subchronic histopathology evaluations).

Rodent Functional Observation Battery

The functional observation battery (FOB) was assessed for all rats in all groups prior to surgery and again prior to scheduled sacrifice at 1, 6, 12, or 24 weeks. Rats were individually placed in a Plexiglas® enclosure fitted with a lid and absorbent paper flooring. Animals were observed for ≥5 minutes for signs of pharmacological or toxicological activity as described by Shayne Gad. Gad S C: Screens in Neurotoxicity: *Objective, Design, and Analysis, with the Functional Observation Battery as a Case Example*, International Journal of Toxicology 1989, 8:287-301. Parameters include posture, ataxia, awareness reaction, body tremors, corneal reflex, abdominal tone, grip strength, respiration, excretion, immobility, secretion, irritability, loss of righting, motor activity, nociceptive response, piloerection, pinnal reflex, pupil size, convulsions, startle response, stereotype behavior, and vocalization.

Spontaneous Motor Activity

Spontaneous Motor Activity was assessed on every animal at baseline and on approximately the day of termination (1, 6, 12, and 24 weeks in respective cohorts). Rats were individually placed in a photobeam activity system (Kinder Scientific, Poway, Calif.) to record spontaneous motor activity over a 20 minute period. This system uses 32 Infrared Beams to quantify 2-Dimensional Ambulation. The data (number of "ambulations") were recorded at four 5 minute intervals within the 20 minute observation period.

Hind Foot Sensory Function/Reflex

An assessment of von Frey filament hind foot withdrawal threshold was conducted on every animal at baseline and on approximately the day of termination (1, 6, 12, and 24 weeks in respective cohorts). Filaments were applied to the paw of the surgical hind limb from underneath the cage through openings in the mesh floor. There are 20 filaments, ranging from a target force of 0.008 grams to 300 grams. The evaluator started with the 0.008 g (weakest stimulus) filament and progressed sequentially until either a response was recorded or 300 g was reached. At each time point, three sets of tests were conducted, with the average force producing a response considered the withdrawal threshold for that animal. Group data are expressed as mean±SD.

Goat Epidural Implantation Model

Mixed Boer Goats (n=144 male and 144 female) were acquired by Thomas D. Morris, Inc. (Reisterstown, Md.). Animals were divided into 16 treatment groups over the course of 6 procedural cohorts. Treatments included a variety of doses delivered using one of three different needle approaches deposit the pellets adjacent to a targeted spinal nerve as well as an intentional misuse approach into the intrathecal space. The numbers of animal in each treatment group were as follows:

Group 1) Untreated Control (n=10 per sex)

Transforaminal Epidural Placement Groups

Group 2) Sham [lidocaine and contrast media only] (n=14 per sex)

Group 3) Placebo [18 pellets] (n=12 per sex)

Group 4) 6×CP-08 pellets, transforaminal [1130 mcg] (n=6 per sex)

Group 5) 6×CP-15 pellets, transforaminal [2000 mcg] (n=14 per sex)

Group 6) 6×CP-15 pellets plus 200 mcg bolus of clonidine HCL, transforaminal [2200 mcg] (n=14 per sex)

Group 7) 18×CP-05 pellets, transforaminal [2200 mcg] (n=14 per sex)

Group 8) 18×CP-08 pellets, transforaminal [3400 mcg] (n=20 per sex)

Group 9) 18×CP-15 pellets, transforaminal [6000 mcg] (n=14 per sex)

Alternative Placement Groups

Group 10) 6×CP-08 pellets, interlaminar epidural [1130 mcg] (n=3 per sex)

Group 11) 6×CP-08 pellets, selective spinal nerve [1130 mcg] (n=3 per sex)

Group 12) 10×CP-08 pellets, interlaminar epidural [1900 mcg] (n=3 per sex)

Group 13) 10×CP-08 pellets, selective spinal nerve [1900 mcg] (n=3 per sex)

Group 14) 6×CP-15 pellets, interlaminar epidural [2000 mcg] (n=6 per sex)

Intentional Misuse Groups

Group 15) 6×CP-08 pellets, intrathecal [1120 mcg] (n=2 per sex)

Group 16) 6×CP-15 pellets, intrathecal [2000 mcg] (n=6 per sex)

Group 1 was a large control group used to assess the variation and natural history of performance on the neurological exams selected for this study in untreated goats. Goats in group 1 were shaved and prepped so as to give the appearance of having undergone the procedure, although the needle was not advanced past the subcutaneous space. This was intended to facilitate the blinding of the examiner. In all treated animals, the most caudal interlumbar level was targeted. For the transforaminal approach (Groups 2-9), the needle was directed towards the most caudal interlumbar foramen on the left side after entering the skin approximately 8-12 cm lateral to the spinous processes. Using fluoroscopic guidance, the needle was advanced into the cranial third of the neuroforamen and beneath the epiradicular membrane, with the tip of the needle superior to the DRG, at the 12 o'clock position with respect to the nerve. Contrast media (Optiray™ 320, Tyco Healthcare) was injected to confirm needle placement, followed by 2 ml of 2% lidocaine and then the appropriate pellet formulation and number of pellets. Group 2, the sham group, received only contrast media and lidocaine and no pellets. A specialized funnel containing the pellets was attached to the hub of the spinal needle for test article delivery. Pellets were driven down the lumen of the needle with a stylet or "plunger" until the pellets were dispensed from the tip of the needle into the target space. In Group 6, the 6×CP-06 pellets were supplemented with a 200 mcg bolus of clonidine (2 mL of 100 mcg/mL solution, Duraclon®, Xanodyne, Inc.). In this case, the bolus of clonidine was given just before pellet placement (to prevent possible displacement of the pellets by the solution as it came out of the spinal needle). The highest pellet loads tested (18 placebo, CP-05, CP-08, or CP-15) were considered to be the theoretical maximum technically achievable dose based on measurements taken in several cadaveric goat lumbar spines. Eighteen pellets completely fills the so called "safe triangle", or the space between the DRG/spinal nerve and the caudal border of the superior pedicle. This space is the standard target for a transforaminal injection. Goodman B, Posecion L, Mallempati S, Bayazitoglu M: *Complications and pitfalls of lumbar interlaminar and transforaminal injections*, Current Reviews in Musculoskeletal Medicine 2008, 1:212-222.

In order to assess the impact of different needle approaches on the target (spinal nerve roots and spinal nerves), two additional approaches were tested: an interlaminar epidural approach (the current proposed clinical approach) through the back of the spinal column and a selective spinal nerve approach where pellets were placed adjacent to the exiting spinal nerve, outside of the epiradicular membrane. For the intelaminar epidural approach (Groups 10, 12, and 14), pellets were placed in the epidural fat in the left lateral recess. The needle was directed to the target interlaminar space using a dorsal approach, entering the skin approximately 2-4 cm lateral to the spinous processes on the left side and slightly caudal to the target. The needle was advanced until the needle tip breached the ligamentum flavum and entered the epidural space. Epidural placement adjacent to the targeted nerve roots was verified by injecting a small volume (<3 mL) of contrast media. Once the needle was correctly positioned, goats first received 2 ml of 2% lidocaine injected into the target site. At this point, the funnel containing the appropriate dose of pellets was connected to the hub of the needle and pellets were dispensed as in the transforaminal approach.

The technique for the selective spinal nerve approach (Groups 11 and 13) is similar to the transforaminal approach, the primary difference being that the tip of the needle does not breach the epiradicular membrane. The spinal needle is directed to the target neuroforamen using a dorsolateral approach, entering the skin approximately 8-12 cm lateral to the spinous processes on the left side. The target area is caudal to the superior pedicle, slightly more caudal and dorsal as compared to the transforaminal approach (3 o'clock position with respect to the nerve from a view with the spinous process on the right). To confirm correct needle placement, a small volume (<3 mL) of contrast media was dispensed through the spinal needle after positioning. In this case, contrast media spreads along the spinal nerve along with diffuse spreading in the tissue around the nerve. Once the needle was correctly positioned, goats first received 2 ml of 2% lidocaine injected into this target site. At this point, the funnel containing the appropriate dose of pellets was connected to the hub of the needle and pellets were dispensed as in the other approaches.

Intentional Misuse

In order to assess the effects of misplacement of the pellets into the intrathecal space, Groups 15 and 16 served as intentional misuse groups. This approach to the intrathecal space was technically similar to the interlaminar epidural approach, except the needle was advanced until it breached the arachnoid membrane. To confirm placement, the needle was repositioned as necessary until CSF began leaking from the hub of the needle. Once a CSF leak was established, contrast media was injected into the intrathecal space. In one case, CSF could not be obtained after repeated attempts and so in this case intrathecal placement was confirmed by imaging alone. Contrast media was followed by 2 ml of 2% lidocaine. Following confirmation of intrathecal placement of the tip of the needle, pellets were dispensed as in the other approaches.

Neurological Function Evaluations

Detailed neurological exams were conducted 24 and 72 hours post-operatively as well as at 1 week, 4 weeks, 8 weeks, 12 weeks, 18 weeks, and 24 weeks (in remaining animals). Neurological exams were designed to assess postural reflexes, perineal reflex, hind limb withdrawal reflexes, hind-limb proprioception, and gait, adapting methods described by Alexander de Lahunta, D V M. Lahunta Ad, Glass E: *Veterinary Neuroanatomy and Clinical Neurology* Edited by St. Louis, Mo., Saunders, 2009. Exams included a general assessment of ambulation and strength, graded on a 0 (normal) to 5 (paralysis) scale as follows:

Grade 0—normal strength and coordination
Grade 1—readily stands and walks with minimal paraparesis and ataxia
Grade 2—able to stand, but with difficulty; often falls but can walk; mild to moderate paraparesis and ataxia
Grade 3—unable to stand unassisted; when assisted, able to move the pelvic limbs but constantly stumbles and often falls; moderate to severe paraparesis
Grade 4—unable to stand unassisted; when assisted only sight pelvic limb movement; severe paraparesis and ataxia
Grade 5—unable to stand unassisted; when assisted complete absence of any pelvic limb movement; paralysis Animals were also graded on postural reflex, withdrawal response, patellar reflex, and anal reflex. Both the right and left sides were scored separately. Reflex scores are graded on a 0 to 4 scale with 2 representing a normal reflex. The grading key for the four reflexes is as follows:

Grade 0—reflex absent
Grade 1—hyporeflexive
Grade 2—normal
Grade 3—hyper-reflexive
Grade 4—spastic Histopathy In both animal models, a comprehensive histological evaluation of the implant site, with emphasis on nerve tissue in contact or near the implants, was conducted. In rats, the sciatic nerve and thigh musculature was processed to paraffin blocks and prepared to slides. Separate slides were stained with hematoxylin and eosin (H&E) for general morphology assessment, luxol fast blue for myelin, Bielschowsky's silver stain for axons, and sciatic nerve cross sections with Spurr's embedding and toluidine blue staining. Graded histopathology end-points included sciatic nerve fiber degeneration, epineurium changes, encapsulation, tissue fibrosis/granulation, and hemorrhage. The implant site (including surrounding muscle tissue) was also graded for neutrophil, eisoinophil, and neutrophil prevalence and formation of giant cells and granuloma.

In goats, the spinal cord, spinal nerve roots/ganglia/nerves, and local muscle were processed and examined. The section of the spinal column containing the spinal nerve roots and spinal nerve at the level of pellet administration as well as one foramen cranial and one foramen caudal was extracted and processed to paraffin blocks and prepared to slides. Similar to the methodology for assessing the rat sciatic nerves, standard H&E staining as well as special stains for nerve were used to assess the spinal cord and spinal nerve roots/ganglia/nerves at all three levels mentioned above. A cross section of all three spinal nerves on the implanted side was prepared with Spurr's embedding and Toluidine blue staining. Non-nerve tissue near the implant site, including adipose tissue and muscle tissue, was assessed using slides stained with H&E. Epidural tissue, the dura, the arachnoid membrane, the spinal cord, spinal nerve roots and spinal nerve, the dorsal root ganglion, and epineurium were separately assessed for inflammation, immunological cell infiltration, hemorrhage, inflammation, and cell degeneration (where applicable) as part of the detailed assessment of nerve tissue local tolerance.

In both models, histopathology was graded on the following 6-point scale:
(0)=None.
(1)=Slight. Affects less than 1% of the tissue. Sporadic and of no relevance to form or function.
(2)=Minimal. Less than 5% of tissue affected. Very unlikely to have any biological relevance.
(3)=Mild. Approximately 5 to 15% of the tissue affected. Unlikely (but possible) to have some biological relevance unless stated otherwise in the pathologist's narrative.

(4)=Moderate. A pronounced change with approximately 15 to 40% of the tissue affected. Possibly or likely to have some effect on structure or function.

(5)=Severe. A very pronounced change with more than 40% of the tissue affected. Very likely to have some structural or functional effect.

For the purpose of summarizing the large amount of histopathology data, the frequency of the various histopathology findings reaching the mild grade (the point at which effects on tissue function are unlikely but possible) are expressed in data tables. Findings graded as slight or minimal are considered to be of no toxicological significance and are not discussed.

Pharmacokinetics

In rodent studies, blood was collected for plasma drug analysis 4 hours post-administration, daily through 1 week post-administration, and weekly thereafter in remaining animals. Following collection, blood samples were chilled on ice (approximately 1500×G for approximately 10 minutes) to separate the plasma. Plasma will then be collected, and stored frozen at approximately −70° C. or lower.

Blood samples were collected at the same time±30 minutes at 4 hours, 1 day, 2 days, 3 days, 5 days, and 7 days, and then weekly throughout the study until termination. At each timepoint, 5 mL of blood was collected in EDTA K2 coated tubes. Each sample was centrifuged at 3000 rpm for 10 minutes. The plasma was separated, frozen, and stored at −70° C. Samples were shipped to PharmaNet Canada, Inc. (Quebec, Canada) for analysis. Clonidine was extracted from an aliquot of pig EDTA K2 plasma using a liquid-liquid extraction procedure, then injected into a liquid chromatograph equipped with a tandem mass spectrometry detector. The quantitation method is by peak area ratio. A weighted (1/C2) linear regression was performed to properly determine the concentration of clonidine in pig plasma. All regressions were generated by MDS Sciex Analyst version 1.4.1 and Thermo Electron Corporation Watson LIMS software version 7.0.0.01b. Methods were validated for determination of clonidine in plasma over an analytical range of 10.0 to 500 pg/mL in the goat and 20.0 to 5010 pg/mL in the rat. In cases where the apparent concentration was above the upper limit of quantification, samples were diluted and re-assayed.

Results

Clonidine pellets (CP-05, CP-08, and CP-15) and placebo pellets were associated with a mild foreign body response in both animal models with no dose-response relationship. In rats, tissue changes at the site of implantation site included minimal to mild fibrosis of the epimysium, granulation around the implant site, encapsulation of implants, muscle fiber degeneration/regeneration, focal nerve fiber degeneration, and mononuclear cell infiltration. The incidence of histopathology scores reaching the mild (grade 3) level was highest at one week, with 17 such findings in the 192 animals. Five animals were found to have both mild perineurium fibrosis and mild perineural mononuclear cell infiltration at 1 week (1 placebo male, 1 female in the 9 XCP-15, 1 female in the 12×CP-15 groups, and 2 males in the 12×CP-15 group. Other mild findings at one week included encapsulation (two 15×CP-08 females), epimysium fibrosis (1 sham male and three 3×CP-08 males), and focal nerve fiber degeneration (one 12×CP-15 female). The number of histopathology parameters reaching the mild grade fell to 4 at 6 weeks, 3 at 12 weeks, and 4 at 24 weeks. These sporadic findings included epimysium fibrosis, perineural mononuclear cell infiltration, one instance of encapsulation, and one instance of perineurium fibrosis. During each of the last three termination points, the incidence of any single mild finding never exceeded one animal per treatment group and there were no cases of mild histopathology parameters in the two highest dose groups (3000 mcg and 4000 mcg Clonidine HCL).

Systemic signs of toxicity were observed at doses that did not have any adverse local effects in animals treated with high doses of CP-08 and CP-15, with respective systemic LOAELs of 2850 ug (CP-08) and −3000 ug (CP-15). No significant systemic effects were noted in animals treated with CP-05 up to the maximum technically achievable dose (1830 ug). Clinical observations included aggressive behavior that was noted during the 1-week functional observation battery in all females and 5/8 males at a dose of 2850 ug CP-08 and in all males at doses of ≥2000 ug CP-15 and 5/8, 1/8, 4/7 females at doses of 2000, 3000 and 4000 ug CP-15, respectively. This aggressive behavior is known to be a unique effect of clonidine in rodent models and is believed to be related to antagonist activity on adenosine receptors at high doses. Fujiwara Y, Takeda T, Kazahaya Y, Otsuki S, Sandyk R: *Inhibitory effects of carbamazepine on clonidine-induced aggressive behavior in mice*, Int J Neurosci 1988, 42:77-84. Animals treated with CP Pellets exhibited decreased activity, particularly during the first week post-implantation at doses of 2000, 3000, and 4000 ug CP-15. This was noted during daily clinical examinations as well as the spontaneous motor activity assay (1 week only, with no trend towards decreased activity versus sham at later time points). Decreased activity was most evident during general clinical observations in the first 72 hours, corresponding to the $T_{max}$ of systemic clonidine (1-3 days in most animals). Clonidine has established, dose dependent, intense sedative effects in man and numerous animal models, including rat. Eisenach J, Detweiler D, Hood D: *Hemodynamic and analgesic actions of epidurally administered clonidine*, Anesthesiology 1993, 78:277-287; Soares de Moura R, Rios A, de Oliveira L, Resende A, de Lemos-Neto M, Santos E, Correia M, Tano T: *The effects of nitric oxide synthase inhibitiors on the sedative effects of clonidine*, Anesthesia and Analgesia 2001, 93:1217-1221. The acute hypo-activity during the first 24 hours is interpreted as an interaction between recovery from anesthesia and the sedative effects of clonidine. The decreased activity during days 2-7, which occurred at a lower frequency and dose dependent fashion as compared to the first 24 hours, is interpreted to be sedative effects of clonidine alone. Abnormal gait and stance during the first 24 hours post-implantation were attributed to recovery from anesthesia.

Changes in food consumption and reduced weight gain following surgery were observed in CP pellet groups but they were not considered toxicologically adverse. Particularly at doses above 1830 ug clonidine HCL, animals showed decreased food consumption during the first week, although during the ensuing three weeks effects were variable and sporadic (some animals had increased food intake versus controls whereas other continued to show decreased food consumption). After four weeks, no changes in food consumption compared to sham controls were noted at any dose. These findings are considered to be of no toxicological relevance. Other clinical observations included a general stress response at doses above the NOAEL, such as sporadic red staining on face, ruffled coat, and urogenitial staining, particularly during the first two weeks post-implantation. Although some of these signs occurred in animals treated with lower doses or in control animals, the frequency of occurrence was higher at the highest doses.

In animals treated with 9×CP-15 (3000 ug) and 12×CP-15 (4000 ug), there were deaths and unscheduled sacrifices attributed to systemic clonidine toxicity, particularly since the timing of the deaths coincided with the peak plasma levels of API. One female in the 9×CP-15 was found dead on the third day post-implantation. Changes observed at necropsy were darkened kidney, liver, spleen, intestines, and uterus as well as distended stomach sometimes with brown and yellow fluid. Since this animal was found dead, it cannot be determined if any or all of the observed changes were post-mortem changes (bloating, post-mortem changes in myoglobin, putrefaction, autolysis, and organ discoloration). In the 12×CP-15 (4000 ug) group, one moribund female was euthanized the day after implantation and one moribund female was terminated on the third day post-implantation. In the same dose group, one female was found dead on the third day post-implantation. Changes observed at necropsy were distended stomach sometimes containing fluid, red discoloration of the mucosa of the stomach, and enlarged adrenal glands. There were no treatment effects on Von Frey sensory function (reflexes in treated versus untreated leg) or the Functional Observation Battery (other than the aggressive behavior noted above).

In the goat model, microscopic findings reaching a mild grade showed no relationship to dose but a possible relationship to the needle approach. Mild epineurium hemorrhage was most common at 1 week, with 9 cases distributed across the transforaminal approach groups (including two sham animals and one placebo animal). Since the rate of mild epineurium hemorrhage in animals treated with test article never exceeded the rate in sham animals, this is considered to be a complication of the procedure. Also at one week, there was one case of mild dural hemorrhage (1/3 placebo males) and one case of mild epineurium inflammation and necrosis necrosis one 18×CP-15 female).

Sporadic nerve fiber degeneration was recorded beginning at the 6 week termination in animals receiving placebo or CP transforaminal injections. At six weeks, three cases of mild nerve fiber degeneration affecting either the dorsal or ventral portion of the spinal nerve (one 6×CP-15 plus 200 ug clonidine HCL bolus male, one 18×CP-08 male, one 18×CP-15 male). Also at six weeks, there were two cases of mild nerve fiber degeneration affecting the dorsal portion of the nerve root (one 18×CP-05 female and one 18×CP-08 male). Four instances of mild nerve fiber degeneration affecting the spinal cord was found in the Intrathecal (misuse group).

Sporadic, mild nerve fiber degeneration was also documented at twelve weeks (four instances affecting the spinal nerve, one case affecting the cauda equina, and two cases affecting the spinal cord) and twenty four weeks (seven cases affecting the spinal nerve and four cases affecting the dorsal nerve root). The rate of mild nerve fiber degeneration did not appear to be affected by dose, but a potential relationship to needle approach was evident. Spinal nerve and/or nerve root degeneration was reported only in animals that were treated using a transforaminal approach. In seven of these animals, one or more pellets were placed within the borders of the nerve, piercing part of the nerve itself. Although this was restricted to the transformaninal needle approach, there was no dose-response relationship with this finding. There were two cases of mild degeneration affecting the spinal cord (one intrathecal female at 12 weeks and one 18×CP-08 female at 12 weeks).

Sporadic (no more than 1 animal per group per time point) mild myofiber degeneration or degeneration/regeneration was recorded with no relationship to dose, approach, or time (data not shown in Tables). Sporadic epimysium hemorrhage reaching a moderate grade was reported at the one week termination (data not shown in Tables). The frequency of para-spinal hemorrhage peaked at one week (10 cases in 54 animals). At the final necropsy, only a single case (in 52 animals) of hemorrhage in or near the implant site was reported. The changes in muscle and other extraneural tissue near the target nerves was interpreted as minor complications of the procedure and not of toxicological relevance.

Neurological function, including performance on reflex (postural, patellar, perineal, and limb withdrawal) and ambulation scores fell within the normal range in all animals and at all-time points with three exceptions across the 288 study animals. There was one female treated with 6×CP-08 using the TF approach that began exhibiting muscle weakness beginning 7 weeks following the injection procedure. This animal became progressively ill and developed anorexia and dehydration. At approximately 9 weeks, this animal was euthanized. An abscess was found on the spinal cord during necropsy. Upon microscopic examination, this abscess was found to have significant mononuclear cell infiltrate and signs of active inflammation affecting the loose epidural tissue adjacent to the cord and causing minimal spinal cord compression and nerve fiber degeneration. No pellets were located in or near the abscess. The abscess is likely the result of a bacterial infection, possibly introduced by the spinal needle during the implantation procedure.

A male in the placebo group developed ataxia and tremor beginning at about 10 weeks post-implantation. Gait was considered to be outside of the normal range, although reflexes were normal. At necropsy 12 weeks post-implantation, no grossly visible abnormalities in the spinal cord, nerve roots, cauda equina, spinal nerve, or brain could be found. Microscopic examination of the implant site did not reveal any damage or abnormalities in the targeted spinal nerve and nerve roots. Extraneural tissue in the vicinity of the implants, including muscle an adipose tissue, appeared normal. There was a slight foreign body response with minimal, focal mononuclear cell infiltrate in the perimysium, but the magnitude of the foreign body response was similar to asymptomatic animals.

The final animal with neurological function falling outside of the normal range was an intentional misuse female (6×CP-08 delivered intrathecally). The morning following implantation (approximately 16 hours post-procedure), this animal was found struggling to ambulate. The animal was observed for two hours, during which time motor function progressively deteriorated. Within 24 hours of the implantation procedure, the animal was euthanized. Spinal cord compression was noted, although no histopathology findings exceeded the mild range. The precise etiology of the rapid neurological deterioration in this animal is unclear. As part of the protocol for intrathecal injection, there is an attempt to obtain a small amount of CSF to confirm that the needle traversed the arachnoid membrane. In this particular animal, CSF did not appear in the hub of the needle despite fluoroscopy images indicating that the needle was correctly positioned. Repeated attempts were made to draw CSF by repositioning the needle within the central canal. It is suspected that the complications of this procedure may have caused the acute neurological dysfunction. Although significant nerve fiber damage was not evident around the implant site, this may be a function of timing. Following injury the spinal cord or cauda equina, it can take as many as seven weeks for nerve fiber degeneration and abnormalities on MR imaging to fully manifest. Becerra J L, Puckett W R, Hiester E D, Quencer R M, Marcillo A E, Post M J, Bunge R P: *MR-pathologic comparisons of wallerian degeneration in spinal cord injury*, AJNR Am J Neuroradiol 1995, 16:125-133.

In both animal models, systemic exposure peaked within the first week post-implantation (FIG. 1). In rodents, $T_{max}$ was typically within the first three days, and often on the first day post-implantation. In goats, $T_{max}$ was typically 1 to 4 hours post-implantation. Plasma drug levels were consistently below the clinical therapeutic range (500 pg/mL to 2 ng/mL) in goats at all doses tested. In rats, however, peak plasma drug levels exceeded the upper end of the therapeutic range (2 ng/mL) in all dosing groups and by more than 10 fold in the high-dose females (Table 1), falling to below 500 pg/mL by the 9th week post implant in all dose groups (FIG. 1 illustrates the PK profile in the highest dose groups in both animal models).

Discussion

Encapsulating drugs in polylactic acid (PLA) and related poly(lactic-co-glycolic acid) (PLGA) is an increasingly common strategy to achieve a sustained release depot. However, there are currently no sustained-release polyester drug depots indicated for delivery adjacent to nerve tissue. This is the first study to specifically assess the effects of Poly(D,L)Lactide on nerve tissue. Excluding instances of mechanical trauma related to the implantation procedure, PLA pellets containing from 0 to 15% clonidine HCL were not found to cause any local toxicity following paraneural placement in rats and goats. In the goats, the highest dose tested (18 CP-15 pellets, total drug load 6000 ug) was considered a maximum technically achievable dose based on the theoretical space available for a one-level transforaminal injection. This dose failed to produce any perceptible systemic effects and failed to even transiently elevate plasma drug concentrations into the accepted therapeutic range. Frisk-Holmberg M: *Clinical pharmacology of clonidine*, Chest 1983, 83:395-397. The antihypertensive effects of clonidine become evident above 500 pg/mL whereas approximately 2 ng/mL is the systemic concentrations associated with spinal analgesia. There was a mild macrophage-driven foreign body response, although no tissue reactions were considered to be adverse. With respect to nerve tissue, PLA pellets with and without clonidine appear to be inert. There was sporadic, mild grade nerve fiber degeneration in the vicinity of the implants in a minority of goats receiving pellets via a transforaminal approach (regardless of dose) but not in animals that received pellets using an interlaminar epidural approach. With both of these approaches, the target is within a few millimeters of the spinal nerve roots and spinal nerve, but in the interlaminar approach the pellets are deposited in the epidural fat within the lateral recess adjacent to the descending and exiting nerve roots whereas in the transforaminal approach the pellets are deposited in the epiradicular space in the bony lateral foramen. It is suspected, therefore, that the association of the transforaminal approach with spinal nerve fiber degeneration is related to the relatively limited space available between the nerve and bony foramen. This results in a limited margin of error for placing the pellets without causing mechanical trauma to the DRG and spinal nerve. Indeed, in seven study animal administered pellets via the transforaminal approach, some pellets were found within the borders of the nerve (piercing the nerve). This occurred in both low dose (6 pellets of CP-15) and high dose (18 pellets CP-08 or CP-15) animals. This was not observed in any of the animals administered pellets via the interlaminar epidural approach, the selective spinal nerve approach, or the intentional misuse intrathecal approach. Therefore, nerve fiber degeneration in these animals is considered to be a result of mechanical trauma incurred during the transforaminal implantation procedure as opposed to a toxic reaction to the test article per se. Regardless of approach, it is believed that misplacement of the pellets within nerve tissue will be much less likely in the clinical setting because the procedure will be conducted under local and not general anesthesia. This allows the patient to provide feedback if the needle approaches a nerve too closely.

The rodent studies support the hypothesis that the sporadic nerve fiber degeneration noted in goats administered pellets by way of a transforaminal approach is a result of mechanical injury as opposed to a reaction to CP or placebo pellets. In rodent studies, there was only a single case of mild focal nerve fiber degeneration near the implantation site out of the 768 study animals. This is isolated finding is considered to be spontaneous and not a reaction to the pellets. Since the pellets are surgically placed adjacent to the sciatic nerve in the rodent model as opposed to the percutaneous delivery used in the caprine model, injury resulting from accidental misplacement of the test article was unlikely. Unlike in the goat model, systemic effects of clonidine, including toxicity and deaths, were documented in the two highest dose groups (3000 ug and 4000 ug). Therefore, the dose of CP appears to be limited by systemic effects of clonidine rather than local adverse tissue effects. Within the confines of the defined paraspinal target area, it was not possible to reach sufficient plasma drug levels to elicit any systemic effects in the goat model. It is surmised, however, that if the target area was expanded to allow higher CP doses in the goat, systemic drug effects would become apparent in the absence of local effects on tissue form or function. Microscopic findings in both animal models demonstrate that paraneural placement of PLA pellets containing up to 15% clonidine HCL, at doses up to the defined maximum technically achievable pellet load in goats and at doses exceeding the systemic NOAEL in rats, results in a minimal to mild macrophage-driven foreign body response with sporadic, benign changes around nerve tissue. Poly(D, L-lactide), with and without clonidine HCL, appears to be well tolerated by nerve tissue in both rats and goats.

TABLE 1

Pharmacokinetics parameters in rats following surgical administration of
PLA pellets containing clonidine HCL. AUC0-t is calculated as the area under the curve from
time zero (implantation) to the last non-zero time point (last time point with a positive drug
signal exceeding the LLOQ of 20 ng/mL). Four animals per group per sex were randomly chosen for analysis.

| | Group # | | | | | | | | | | | | | | | | | | | | | |
|---|---|---|---|---|---|---|---|---|---|---|---|---|---|---|---|---|---|---|---|---|---|---|
| | 1 | | 2 | | 3 | | 4 | | 5 | | 6 | | 7 | | 8 | | 9 | | 10 | | 11 | |
| | Treatment | | | | | | | | | | | | | | | | | | | | | |
| | Sham | | 12 × Placebo | | 15 × Placebo | | 3 × CP-08 | | 3 × CP-15 | | 6 × CP-08 | | 15 × CP-05 | | 6 × CP-15 | | 15 × CP-08 | | 9 × CP-15 | | 12 × CP-15 | |
| | Dose (mcg) | | | | | | | | | | | | | | | | | | | | | |
| | 0 | | 0 | | 0 | | 570 | | 1000 | | 1140 | | 1830 | | 2000 | | 2850 | | 3000 | | 4000 | |
| | Sex | | | | | | | | | | | | | | | | | | | | | |
| | M | F | M | F | M | F | M | F | M | F | M | F | M | F | M | F | M | F | M | F | M | F |
| $C_{max}$ (ng/mL) | — | — | — | — | — | — | 2.5 | 4.5 | 4.1 | 7.1 | 5.7 | 5.5 | 5.1 | 5.9 | 8.9 | 16.4 | 12.5 | 16.4 | 14.1 | 23.7 | 15.7 | 28.8 |
| Tmax (day) | — | — | — | — | — | — | 1 | 1 | 1 | 1 | 1 | 7 | 1 | 2 | 1 | 1 | 1 | 2 | 3 | 1 | 2 | 2 |
| $AUC_{0-t}$ (ng · Day/mL) | — | — | — | — | — | — | 18 | 42 | 45 | 92 | 29 | 89 | 54 | 121 | 106 | 197 | 98 | 231 | 162 | 275 | 218 | 377 |

TABLE 2

Pharmacokinetics parameters in goats following surgical administration of
PLA pellets containing clonidine HCL. AUC0-t is calculated as the area under the curve from
time zero (implantation) to the last non-zero time point (last time point with a positive drug
signal exceeding the LLOQ of 20 ng/mL). Four animals per group per sex were randomly chosen for analysis.

| | Treatment | | | | | | | | | | | | | |
|---|---|---|---|---|---|---|---|---|---|---|---|---|---|---|
| | Sham | | 18 × Placebo (TF) | | 6 × CP-08 (TF) | | 6 × CP-15 (TF) | | 6 × CP-15 plus 200 mcg bolus (TF) | | 18 × CP-05 (TF) | | 18 × CP-08 (TF) | | 18 × CP-15 (TF) | |
| | Dose (mcg) | | | | | | | | | | | | | |
| | 0 | | 0 | | 1130 | | 2000 | | 2200 | | 2200 | | 3400 | | 6000 | |
| | Sex | | | | | | | | | | | | | |
| | M | F | M | F | M | F | M | F | M | F | M | F | M | F | M | F |
| $C_{max}$ (pg/mL) | — | — | — | — | 67 | 95 | 97 | 139 | 71 | 102 | 174 | 235 | 262 | 241 | 279 | 409 |
| Tmax (hours) | — | — | — | — | 1 | 1 | 1 | 1 | 0.50 | 0.25 | 1 | 1 | 1 | 1 | 1 | 1 |
| $AUC_{0-t}$ (pg · Day/mL) | — | — | — | — | 26 | 21 | 280 | 280 | 140 | 57 | 210 | 250 | 109 | 192 | 1100 | 1270 |

Example 2

Polymer Degradation Study in Rats

One year a polymer degradation study assessed systemic and local tolerance with histopathology completed following pellet degradation at 52 weeks. In this study, MDT-05, MDT-08, and MDT-15 were administered to rats using the same para-sciatic placement applied in all rodent studies.

TABLE 3

Dose, Formulation and Method of Administration by Group

| Group | Total Dose | Formulation | Method of Administration |
|---|---|---|---|
| 1 | 1830 ug | MDT-05 | Surgical placement of 15 pellets adjacent to the sciatic nerve |
| 2 | 2830 ug | MDT-08 | Surgical placement of 15 pellets adjacent to the sciatic nerve |
| 3 | 3660 ug | MDT-15 | Surgical placement of 10 pellets adjacent to the sciatic nerve |
| 4 | 5490 ug | MDT-15 | Surgical placement of 15 pellets adjacent to the sciatic nerve |

The dose of MDT-15 in the polymer degradation study was reduced from 5490 ug (first 12 males and 12 females) to 3660 ug (final 6 males and 6 females) following signs of systemic toxicity at the higher dose. All animals treated with MDT-15 and carried out to the one year termination time point received the 3660 ug dose (including 3 animals per sex for pellet degradation and 3 animals per sex for histopathology). All animals treated with MDT-15 and terminated at 36 weeks and earlier received the higher, 5490 ug dose.

Local tolerance was assessed at the site of implantation after complete disappearance of the MDT pellets. Changes in polymer molecular weight and appearance of the pellets were recorded during this study to evaluate the degradation profile of the MDT Pellets and the results are presented herein.

Fifteen pellets of MDT-05, MDT-08, and MDT-15 were surgically placed in the intermuscular space adjacent to the sciatic nerve in Sprague Dawley rats (n=18 males and 18 females per dosing group). Due to systemic toxicity noted in animals, and especially females, treated with 15 pellets of MDT-15, the final 6 animals per sex in that dosing arm received only 10 of the MDT-15 pellets. These 6 animals per sex were all carried out to the final termination point (n=3/sex for pellet degradation and n=3/sex for end-of-study histopathology). MDT pellets were collected from 3 rats per sex at 6, 12, 24, 36, and 52 weeks (although pellets could not be retrieved in most cases at 52 weeks). Animals were assessed at each time point for evidence of pellet remnants. Characteristics such as swelling, rounding, curving, and breaking of pellets indicating hydration/degradation were noted at each time point.

One female was found moribund in the 5490 of dose group and euthanized on Day 5. Changes at necropsy included distended stomach and intestines. In the same dose group, two females were found dead on Day 5. Changes at necropsy included the general appearance of autolyzed tissues. A cause of death was not included in these reports. However, it is suspected that deaths were related to systemic cardiorespiratory effects of clonidine.

There were other unscheduled sacrifices and deaths that were not believed to be related to MDT pellets. A male treated with 3660 ug was euthanized on Day 134 due to ruptured mass (tumor) on the flank and had several significant changes in hematology and serum clinical chemistry parameters. An additional male in the same dose group was found dead on day 353 with no changes at necropsy. A female treated with 2850 ug was found dead on day 358 also without changes at necropsy. These findings are believed to be incidental findings, unrelated to treatment. The active drug is undetectable (<20 pg/mL) in almost all cases past day 90 with all formulations. There was an additional male rat treated with MDT-08 (570 ug) found dead on day 42. Although this death occurred during the time when systemic clonidine is still detectable in most animals, no remarkable findings were noted on necropsy and given the lack of dose-response (lowest does tested), it is believed to be an incidental occurrence expected in a large population of animals and unrelated to the treatment.

In conclusion, MDT pellets at a total dose level of 5490 ug produced clinical signs of effect in both male and female rats including associated deaths in three female rats on day 5. Initial signs of pellet degradation were visible at 24 weeks post-implantation, there was no remaining evidence of pellets in the majority of rats, and those few rats had what appeared to be pellet remnants had no discernible intact pellets remaining.

Surgical procedures and pellet explantation were performed at Calvert Laboratories, Inc. Following tissue collection at Calver, local histology was conducted at Tox Path Specialists, LCC. The weight average (Mw) analysis of explanted MDT pellets was conducted by Medtronic Ventures and New Therapies.

Figure 3:
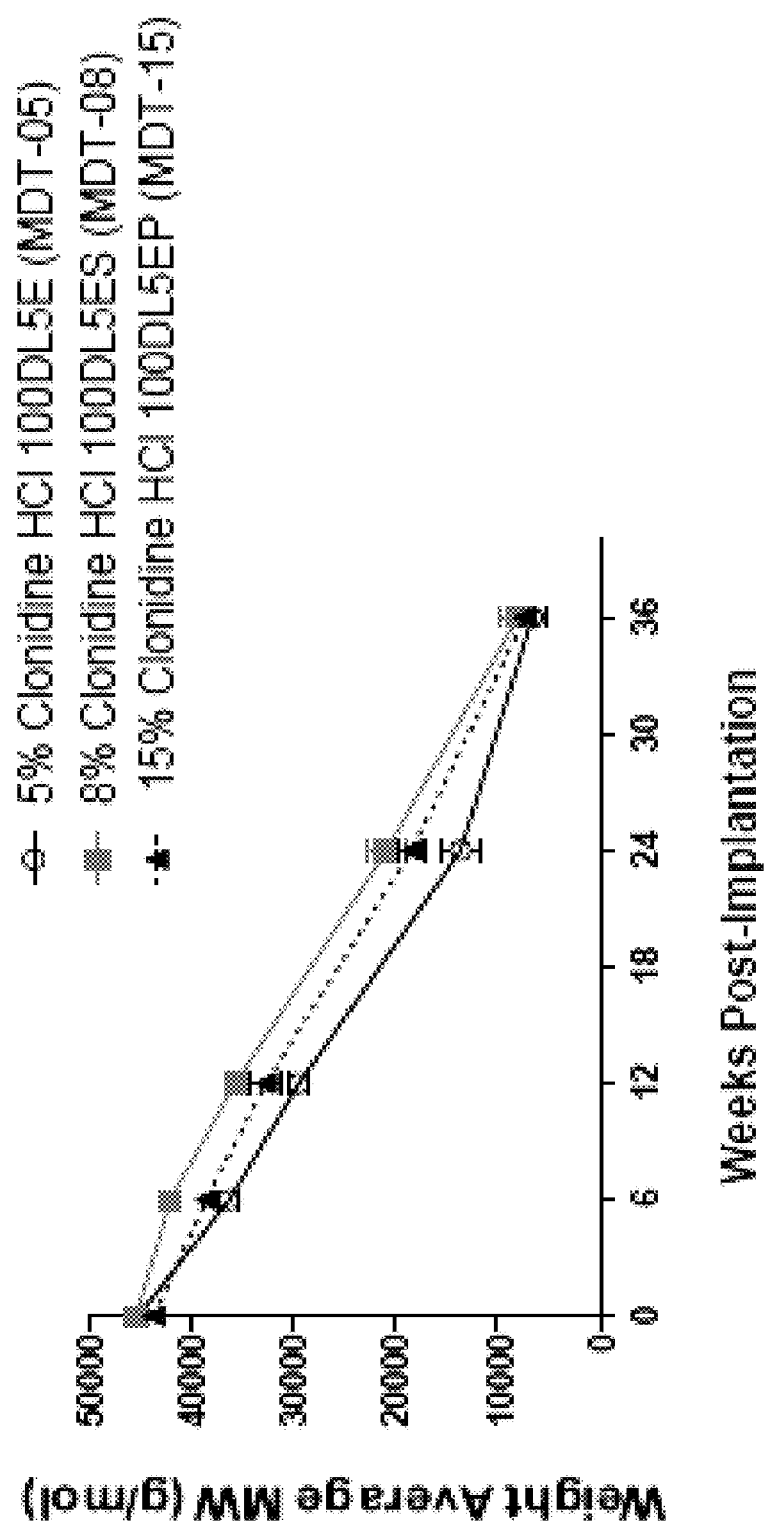
FIG. 3 is a graphic illustration of in vitro average molecular weight of clonidine for over 36 days employing formulations of the present application.

MDT pellets were also analyzed by gel permeation chromatography (GPC) at each time point except 52 weeks due to a lack of material. Weight average molecular weight for three pellet samples of MDT-05, MDT-08, and MDT-15 was recorded before implantation: 45705 g/mol, 45670 g/mol, and 43829 g/mol, respectively. After 24 weeks, the Mw average was 15405 g/mol, 22664 g/mol, and 19789 g/mol, respectively. At the 36 week time point, the Mw average of the samples was 5357 g/mol, 6247 g/mol, and 6835 g/mol, respectively. By the 36 week termination, it was difficult to discern individual MDT pellets, indicating later stages of pellet degradation. At 52 weeks, 82% of the rats sampled had no visible MDT pellets remaining. These findings indicate MDT pellets degraded markedly between 36 and 52 weeks and were ultimately resorbed by the animal. FIG. 3 shows the average molecular weight from the 52 week in vivo polymer degradation study. The clonidine depots had clonidine HCL at 5%, 8%, and 15% loads in poly(D,L-lactide) 95% by weight, 92% by weight, and 85% by weight. The polymers had ester end caps and inherent viscosity in the range of about 0.4 to 0.6 dL/g. The average MW was between 40,000 and 50,000, which stayed above 10,000 for about 36 weeks.

Example 3

The following table illustrates exemplary clonidine formulations for treatment of chronic conditions.

TABLE 4

| Formulation | Inherent viscosity | Pellets | Burst release (24-48 hours) | Cumulative release | Particle size (80% of particles) | Daily release |
|---|---|---|---|---|---|---|
| 95% poly(D,L-lactide)/5% clonidine HCL | 0.45-0.55 DL/g | 0.75 mm × 4.0 mm (diameter and length) | <10% 10-40 mcg in 24 hours | 50% remaining after 60 days | 5-150 μm | 0.5-5 μg/day |
| 92% poly(D,L-lactide)/8% clonidine HCL | 0.45-0.55 DL/g | 0.75 mm × 4.0 mm | <10% or 5-6 mcg/ 24 hours | 50% remaining after 32-40 days 20% remaining after 70 days | 5-150 μm | 1-20 μg/day for 50 days 0.1-10 μg/day after 70 days |
| 85% poly(D,L-lactide)/15% clonidine HCL | 0.45-0.55 DL/g | 0.75 mm × 4.0 mm | <10% | 20% remaining after 35 days 0% remaining after several months | 5-150 μm | 20-150 μg/day for first 24 hours 5-80 μg/day after 24 hours 0.1-5 μg/day after 30 days |

The formulations, in some embodiments, have an ester end group and the polymer has a MW of about 70,000 daltons.

Example 4

Pharmacokinetic Profile of Clonidine

Figure 2:
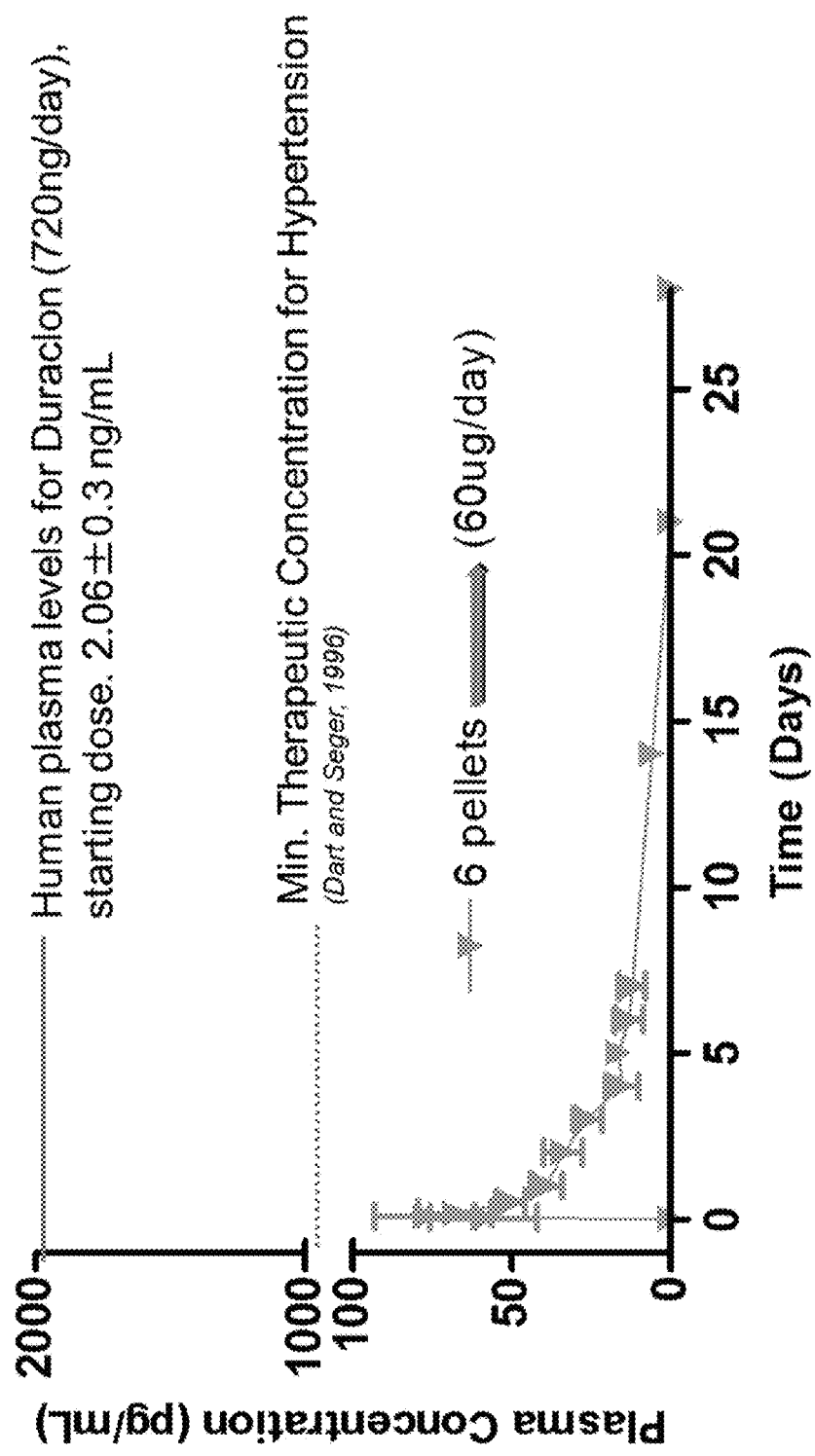
FIG. 2 is a graphic illustration of plasma concentrations of clonidine for over 25 days employing formulations of the present application.

FIG. 2 illustrates the different plasma levels obtained by different formulations. IV Duraclon®, oral clonidine dosed for hypertension and the clonidine formulations of the current application of clonidine 15% with poly(D,L-lactide) having an inherent viscosity of 0.4-0.6 dl/g and a MW of about 50,000 to 70,000 daltons. The burst release was less than 10% and the drug depot released 10 mcg/day for at least 22 days. The graph shows six pellets implanted that can triangulate the wound and be useful in chronic conditions like sciatica. In the first 24 hours there are about 30 mcg per pellet released in the first day. This will be useful to provide immediate relief. The next days there are constant release of clonidine for about one month. The systemic drug levels are approximately 10-20 times lower compared to present depots.

Example 5

Local Toxicity in Goats and Rats 6-18 pellets were injected using three approaches in goats: interlaminar epidural, transforaminal epidural, and selective spinal nerve. All approaches appear to be well tolerated in the goats.

3-15 pellets of clonidine in the depot were surgically implanted in an intermuscular pocket proximal to the sciatic nerve in rats. No local tissue reaction. High doses (>6 mg/kg in rats equivalent to >200 pellets in humans) exhibit systemic signs of stress during the first week (hypo-activity and irritability). However, no toxicity or local irritation was noted indicating that clonidine is safe when given locally in a depot.

Having now generally described the invention, the same may be more readily understood through the following reference to the following examples, which are provided by way of illustration and are not intended to limit the present invention unless specified.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method for treating chronic pain in a patient in need of such treatment, the method comprising administering an implantable drug depot to a target tissue site beneath the skin of the patient, the implantable drug depot comprising clonidine hydrochloride in an amount from about 5.0 wt % to about 20 wt % of the implantable drug depot, and at least one biodegradable polymer in an amount from about 80 wt % to about 95 wt %, wherein the implantable drug depot has a surface that releases a burst dose of the clonidine hydrochloride in an amount from about 5 wt % to about 20 wt % based on the total weight of the clonidine hydrochloride in the drug depot within 24 hours, and the biodegradable polymer is poly(D,L-lactide) and has an inherent viscosity of from about 0.45 dlg to about 0.55 dlg and the implantable medical device releases the clonidine hydrochloride over a period of at least 14 days.

2. A method of treating chronic pain according to claim 1, wherein the chronic pain is caused by sciatica.

3. A method of treating chronic pain according to claim 2, wherein the drug depot triangulates the target tissue site.

4. A method of treating chronic pain according to claim 1, wherein the drug depot is administered at or near the spine.

5. A method of treating chronic pain according to claim 1, wherein the implantable drug depot comprises a length from about 0.5 mm to 50 mm and a diameter from about 0.01 to about 4 mm.

6. A method of treating chronic pain according to claim 1, wherein the implantable drug depot is a solid.

7. A method of treating chronic pain according to claim 1, wherein the implantable drug depot comprises about 15 wt % of clonidine hydrochloride, about 85 wt % of the poly (D,L-lactide) having an inherent viscosity of about 0.5 dL/g, and the surface releases a burst dose from about 5 wt % to about 10 wt % of the clonidine hydrochloride based on the total weight of the clonidine hydrochloride in the drug depot within 24 hours.

8. A method of treating chronic pain according to claim 1, wherein the implantable drug depot further comprises mPEG.

9. A method for treating pain in a patient in need of such treatment, the method comprising administering an implantable drug depot to a target tissue site beneath the skin of the patient, the implantable drug depot comprising clonidine hydrochloride in an amount from about 5.0 wt % to about 20 wt % of the implantable drug depot, and at least one biodegradable polymer is poly(D,L-lactide) in an amount from about 80 wt % to about 95 wt %, and has an inherent viscosity of from about 0.45 dL/g to about 0.55 dL/g, wherein the implantable drug depot has a surface that releases a burst dose of the clonidine hydrochloride in an amount from about 5 wt % to about 20 wt % based on the total weight of the clonidine in the drug depot within 24 hours, and the implantable medical device releases the clonidine hydrochloride over a period of at least 14 days.

\* \* \* \* \*

UNITED STATES PATENT AND TRADEMARK OFFICE
CERTIFICATE OF CORRECTION

PATENT NO. : 9,610,243 B2
APPLICATION NO. : 13/841481
DATED : April 4, 2017
INVENTOR(S) : Clay et al.

It is certified that error appears in the above-identified patent and that said Letters Patent is hereby corrected as shown below:

In the Specification

In Column 12, Line 10, delete "papavereturn," and insert -- papaveretum, --, therefor.

In the Claims

In Column 50, Line 12, in Claim 1, delete "0.45 dig to about 0.55 dig" and insert -- 0.45 dL/g to about 0.55 dL/g --, therefor.

Signed and Sealed this
Tenth Day of April, 2018

Andrei Iancu
*Director of the United States Patent and Trademark Office*